US008500275B2

(12) United States Patent
Yoo et al.

(10) Patent No.: US 8,500,275 B2
(45) Date of Patent: Aug. 6, 2013

(54) VISION TESTING AND/OR TRAINING USING ADAPTABLE VISUAL INDICIA

(75) Inventors: Herb Yoo, Beaverton, OR (US); Alan W. Reichow, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 13/472,807

(22) Filed: May 16, 2012

(65) Prior Publication Data

US 2012/0229760 A1  Sep. 13, 2012

Related U.S. Application Data

(63) Continuation of application No. 12/534,685, filed on Aug. 3, 2009, now Pat. No. 8,197,065.

(51) Int. Cl.
*A61B 3/00* (2006.01)
*A61B 3/02* (2006.01)

(52) U.S. Cl.
USPC .......................................... 351/203; 351/239

(58) Field of Classification Search
USPC .................................................. 351/203, 239
See application file for complete search history.

(56) References Cited

U.S. PATENT DOCUMENTS

| | | | |
|---|---|---|---|
| 3,861,790 A | 1/1975 | Tamura | |
| 4,298,253 A | 11/1981 | Tagnon | |
| 5,050,982 A | 9/1991 | Meissner | |
| 5,363,154 A | 11/1994 | Galanter | |
| 5,478,239 A | 12/1995 | Fuerst et al. | |
| 6,203,157 B1 | 3/2001 | Lee | |
| 6,755,525 B2 | 6/2004 | Reichow et al. | |
| 6,811,258 B1 | 11/2004 | Grant | |
| 6,893,127 B2 | 5/2005 | Reichow et al. | |
| 7,073,208 B2 | 7/2006 | Penque, Jr. et al. | |
| 7,367,675 B2 | 5/2008 | Maddalena | |
| 7,470,026 B2 | 12/2008 | Kaido | |
| 2005/0108661 A1 | 5/2005 | Deeds | |
| 2007/0121066 A1* | 5/2007 | Nashner | 351/210 |

OTHER PUBLICATIONS

Reichow, et al., "Introduction to Behavioral Optometry", Sports Vision, 1993, 75 pages, Optometric Extension Program Foundation, United States.

Ferreira, "An Overview of Research in Sports Vision: its History and an Optometric Perspective", The South African Optometrist, Dec. 2003, pp. 142-149, vol. 62, No. 4, Auckland Park, South Africa.

(Continued)

*Primary Examiner* — Mahidere Sahle
(74) *Attorney, Agent, or Firm* — Shook Hardy & Bacon L.L.P.

(57) ABSTRACT

The present invention tests and/or trains the visual sensitivity of a subject using adaptable visual indicia. One or more visual indicia possessing a visual trait are displayed to the subject. The displayed visual indicia possessing a visual trait may be adjusted to determine when a subject can and cannot be perceived by the subject. A displayed visual indicia may be adjusted in its size, rate of movement, direction of movement, location of display, duration of display, or other characteristic. To determine whether a subject correctly perceived the visual trait possessed by a displayed visual indicia, an input may be received from the subject. If an input received corresponds to the visual trait possessed by the displayed visual indicia, the subject may be determined to have correctly perceived the displayed visual indicia and the visual trait.

14 Claims, 20 Drawing Sheets

OTHER PUBLICATIONS

Coffey, et al., "Visual Performance Enhancement in Sports Optometry", Sports Vision 1995, pp. 158-177, Butterworth-Heinermann, United States.

Cardall, "Contact Lenses in Sport: a General Overview", Optician, Jan. 13, 2006, pp. 22-25, vol. 231, No. 6034, United States.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Koenig, "Practicing Perception: Eyes Can Be Trained to be More Effective", USA Today Baseball Weekly, 1996, 3 pages, United States.

Coffey, et al., "Optometric Evaluation of the Elite Athlete," Problems in Optometry, Mar. 1990, pp. 32-59, vol. 2, No. 1, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

International Search Report and Written Opinion, International Application Oct. 6, 2010 for PCT/US2010/044259.

Non Final Office Action of Apr. 24, 2012 for U.S. Appl. No. 12/534,685.

Final Office Action of Oct. 18, 2011 for U.S. Appl. No. 12/534,685.

Notice of Allowance of Feb. 15, 2012 for U.S. Appl. No. 12/534,685.

\* cited by examiner

VISION TESTING AND/OR TRAINING USING ADAPTABLE VISUAL INDICIA

CROSS-REFERENCE TO RELATED APPLICATIONS

This application is a Continuation of U.S. patent application Ser. No. 12/534,685, filed Aug. 3, 2009, and entitled "VISION TESTING AND/OR TRAINING USING ADAPTABLE VISUAL INDICIA," the entirety of which is incorporated by reference herein.

TECHNICAL FIELD

The present invention relates to testing and/or training the visual sensitivity of a subject. More particularly, the present invention relates to using adaptable visual indicia to test the visual sensitivity, such as static and/or dynamic visual acuity, of a subject.

BACKGROUND OF THE INVENTION

Accurately assessing the visual acuity of an individual is important for a number of purposes. Of course, an accurate assessment of the visual acuity of a subject is a prerequisite to successfully prescribing corrective eyewear for an individual. Additionally, however, assessing the visual abilities of an individual accurately may be critical to determining a training regiment for an individual to improve the visual abilities of the individual, vision testing may even be important to determine what activities an individual should be allowed to engage in, for example, to determine whether an individual may work as a commercial airplane pilot.

Often, visual acuity is assessed using eye charts or eye chart like arrangements. For example, the individual whose visual acuity is being tested may be instructed to read letters or other visual indicia off of a chart located at a predetermined distance from the individual having indicia of varying sizes to determine the smallest size indicia the individual may correctly perceive at a given distance. While such an arrangement has served the eye care industry well, some circumstances do not permit the ready use of such an arrangement. For example, physical space is required to place a subject at a sufficient distance from an eye chart. Moreover, the use of an eye chart using language based indicia, such as letters of an alphabet, can make assessing the visual abilities of illiterate individuals or non-native speakers difficult or impossible. Also, the crowding of multiple indicia on a single chart can cause difficulties unrelated to basic static visual acuity for individuals with unsteady fixation. Further, a typical eye chart arrangement tests only the static visual acuity of an individual, in that the indicia presented are stationary relative to the subject. In real life situations, such as driving or participating in athletic activities, dynamic visual acuity, where an object or indicia is moving relative to the subject, becomes critical to the effective performance of the individual. However, a traditional eye chart assessment does not measure the dynamic visual acuity of a subject.

Beyond visual testing, visual training, while known to be useful in some applications, has similarly been difficult to implement effectively and efficiently. Often, vision testing and vision training may use similar or even identical equipment and/or methods.

BRIEF SUMMARY OF THE INVENTION

The present invention permits the testing and/or training of the visual sensitivity of an individual by using adaptable visual indicia. In accordance with the present invention, an adaptable indicia may be used to test and/or train visual sensitivity abilities such as static visual acuity. For example, an indicia may be presented to a subject on a display device at an initial size that is visually unable to be correctly perceived by the subject. The indicia may then increase in size until the subject correctly perceives the indicia. By presenting a series of indicia and receiving responses from the subject when those indicia may be correctly perceived, an accurate assessment of the static visual acuity of a subject may be made as part of vision testing and/or training.

Visual indicia presented to a subject may possess visual traits. For example, a presented visual indicia maybe be a Landolt C possessing an orientation of left, right, up or down. When a subject perceives the orientation of a presented Landolt C, the subject may create an input to a testing system. For example, the subject may push a joystick in a direction corresponding to the orientation of a Landolt C presented as a visual indicia. By way of further example, a subject may use a multi-touch device to "stroke" the touch-sensitive screen in a direction corresponding to the orientation of a presented Landolt C. By correlating the size of the Landolt C at the time the subject correctly input the perceived orientation of the Landolt C, the visual acuity of the subject may be measured as part of vision testing and/or training.

In accordance with the present invention, the dynamic visual acuity of a subject may be similarly assessed as part of vision testing and/or training. Indicia may move across a display device at varying rates of speed within view of the subject. The subject may indicate for each visual indicia whether the subject has correctly perceived the indicia. For example, each moving indicia presented may possess a trait, and the subject may generate an input based upon the subject's perception of that trait. By varying the speed and/or direction at which displayed indicia move and correlating the correct responses of a subject to the speed and/or direction of the indicia for which the correct response was given, an assessment of the dynamic visual acuity of a subject may be made.

The present invention also may be used to test and/or train the visual target capture abilities of a subject. Indicia possessing visual traits may be presented on a display device, and the subject may attempt to visually acquire the indicia with a saccadic eye movement and perceive the visual trait possessed by the indicia. The location, size, and/or duration of display for an indicia may be varied in accordance with the present invention.

In testing and/or training the dynamic visual acuity and/or visual target capture ability of a subject, a prior determination of the static visual acuity of the individual may be beneficial. For example, an assessment of the static visual acuity abilities of a subject may indicate that the subject cannot accurately perceive static visual indicia below a first size. Based upon that information, the indicia size used for testing the dynamic visual acuity of that subject may be set at the first size or larger, as an individual typically cannot accurately perceive a moving or briefly appearing indicia of a size less than the minimum size of static indicia that the individual can perceive.

In testing and/or training the dynamic visual acuity of a subject, the visual trait possessed by a moving indicia may be constant or varying. For example, a moving Landolt C may maintain its orientation the entire time it is displayed on a display device. Alternatively, a Landolt C may "tumble" by changing its directional orientation as it moves across a display device. The response of the subject may then be correlated to the orientation of the Landolt C at the time the input was received or immediately prior, or alternatively a visual or other sensory indicator may be used to indicate at what point in the motion of the indicia across the display device the individual should access the visual indicia and its trait(s). For example, at a certain point in the movement of a Landolt C across a display device, a sound may be generated or a box may be displayed around the Landolt C, and at that point in time the subject should input the Landolt C's then existing orientation.

By testing and/or training the visual sensitivity of a subject using adaptable indicia on a display device, a visual acuity testing and/or training system may require significantly less space than a conventional eye chart arrangement. Additionally, the testing and/or training equipment required for such a system may be readily transported to locations that might otherwise not be amenable to visual acuity testing. Yet a further advantage of the present invention is that dynamic visual acuity and/or visual target capture abilities may be directly tested and/or trained with the same testing system as is used for testing and/or training static visual acuity. The use of assessment data for static visual acuity to better effectuate testing and/or training of dynamic visual acuity and/or visual target capture abilities further simplifies the visual testing process in accordance with the present invention.

Additional objects, advantages, and novel features of the invention will be set forth in part in the description which follows, and in part will become apparent to those skilled in the art upon examination of the following, or may be learned by practice of the invention.

BRIEF DESCRIPTION OF THE SEVERAL VIEWS OF THE DRAWING

The present invention is described in detail below with reference to the attached drawing figures, wherein.

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combination of steps similar to the ones described in this document, in conjunction with other present or future technologies.

The present invention uses indicia with changing, or adaptable, characteristics to assess the visual sensitivity of a subject. The characteristics possessed by an indicia when an individual can correctly perceive the indicia may provide an indication of the visual sensitivity of the individual. Examples of the types of adaptable characteristics that an indicia may possess in accordance with the present invention are, for example, the size and speed of an indicia. Further examples of changing characteristics are an indicia may possess are different trajectories of movement, color, contrast with a background, duration of display, or any other characteristic that is subject to modification in testing and/or training. In general, systems and methods in accordance with the present invention may use a display device to present indicia that possess varying characteristics, with the characteristics of the indicia potentially varying during any given period of display, to be perceived by a subject. Upon receipt of an input from the subject indicating that the subject believes he or she has perceived the indicia, the input received from the subject may be examined to determine whether it corresponds to the correct input for a displayed indicia. For example, the subject may be provided with an input device capable of receiving any one of a plurality of inputs, with each possible input corresponding to a trait potentially possessed by a displayed indicia. A trait possessed by an indicia may be, for example, an orientation, an identity, etc. By determining whether the input received matches the trait of the indicia displayed, a system in accordance with the present invention may assess the accuracy of the subject's visual perception of the displayed indicia.

Figure 1:
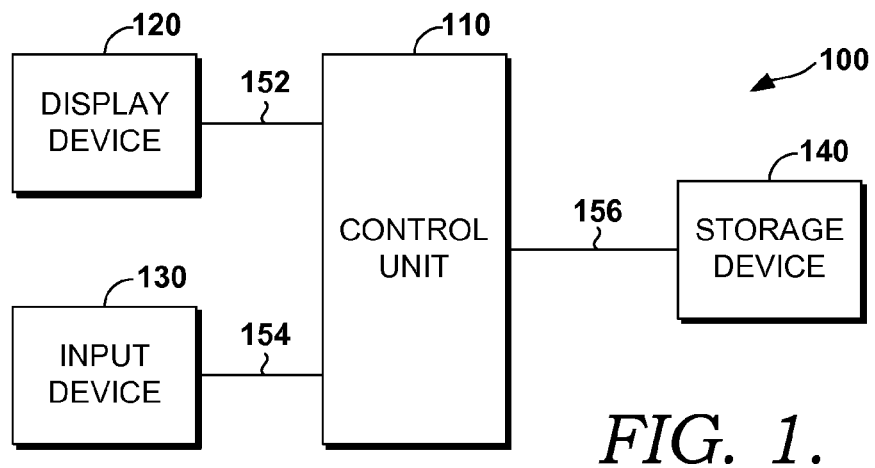
FIG. 1 illustrates schematically a system in accordance with the present invention.

Referring now to FIG. 1, a system 100 in accordance with the present invention is illustrated. System 100 may include a control unit 110. Control unit 110 may comprise any type of computing device. Control unit 110 may further comprise multiple computing devices performing its various functions, as further described herein. Control unit 110 may connect to display device 120 via connection 152. Connection 152 may be any type of wired or wireless connection. Display device 120 may comprise any type of monitor or projection system, including LCD displays, televisions, projectors and screens, display goggles, perspective visual tunnels, or any other type of device capable of displaying a visual indicia that may be perceived by a subject. Control unit 110 may operate to control the indicia displayed on display device 120 and the properties possessed by any displayed indicia.

System 100 may further include input device 130 connected to testing unit 110 via connection 154. Connection 154 may comprise any type of wired or wireless connection. Input device 130 may be any type of device or combination of devices capable of receiving an input from a subject. Examples of acceptable input devices include multi-touch devices, joysticks, buttons, foot pedals, gesture recognition systems, voice recognition systems, and any other type of device. Further, display device so may comprise any type of touch sensitive screen, thereby permitting the single touch sensitive screen to comprise both a display device 120 and input device 130. Input device 130 may operate to receive from a subject a given plurality of possible inputs. For example, a joystick may be utilized as input device 130, which may be manipulated either up, down, left or right. As described more fully in U.S. patent application Ser. No. 12/534,605a multi-touch device may be used as an input device. Similarly, a limited number of arrow keys, letter keys, colored buttons, and the like may be utilized as part of input device 130. Optionally, each of a plurality of possible inputs via input device 130 may correspond to a visual trait of a potentially displayed indicia on display device 120. Control unit 110 may assess an input received from input device 130 as compared to an indicia displayed on display device 120 to determine whether the received input correctly corresponds to the displayed indicia. The position of input device 130 relative to display device 120 may effectively define a distance between the subject and a displayed indicia, although mirrors and/or lenses may also be used to increase or decrease the visual distance between the subject and a displayed indicia.

System 100 may further include a storage device 140. Storage device 140 may be connected to control unit 110 via connection 156. Connection 156 may be any type of wired or wireless connection. Storage device 140 may comprise any type of computer storage medium, such as a hard drive, flash memory, floppy disks, CDs, DVDs or the like. Control unit 110 may utilize storage device 140 to store testing and/or training data generated by a subject. Testing and/or training data may include, for example, the number of correct inputs received from input device 130, the characteristics, such as size or speed or duration of display, of indicia displayed on display device 120 when correct and/or incorrect response(s) were received from input device 130, and various analyses of such data. One of skill in the art will appreciate that storage device 140 may be integral to control unit 110, or may be an entirely separate structure. Similarly, one of skill in the art will appreciate that the various aspects of control unit 110 may be performed by multiple computing devices, rather than a single device, as illustrated in FIG. 1.

Figure 2A:
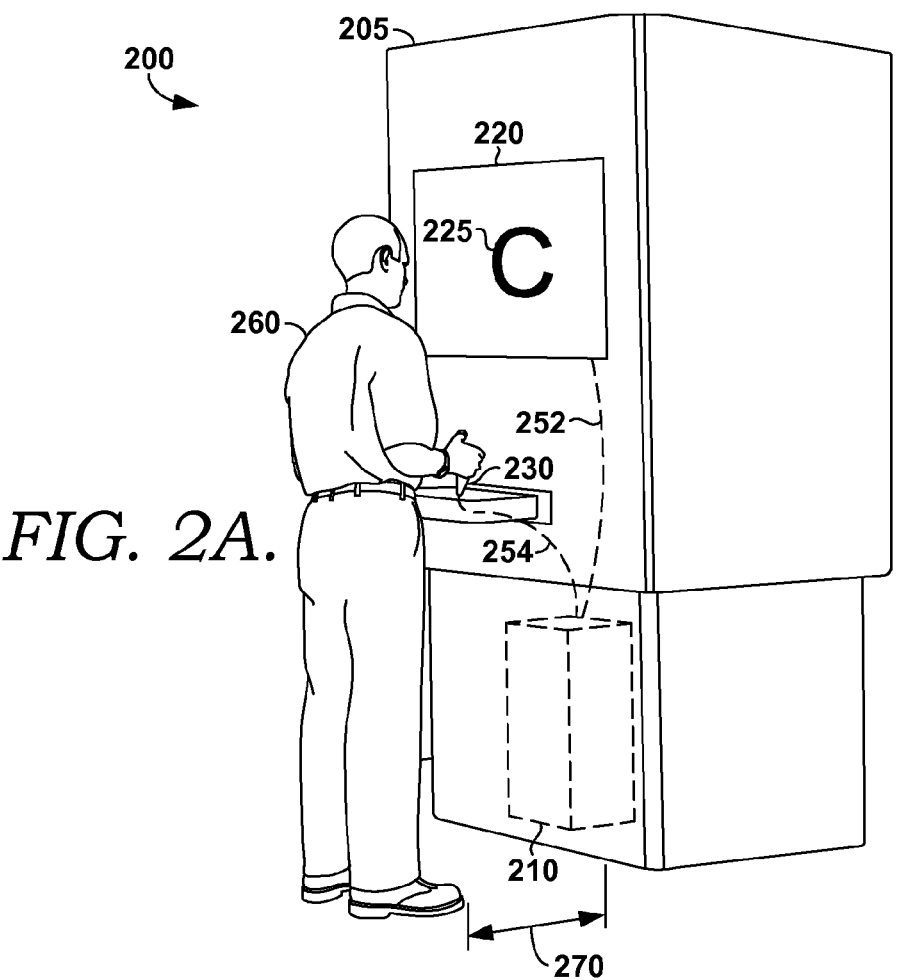
FIGS. 2A and 2B illustrate in a perspective view examples of systems in accordance with the present invention.

Referring now to FIG. 2A, an example of a system 200 in accordance with the present invention is illustrated. System 200 may utilize a kiosk 205 to contain some or all of the components of system 200. System 200 may include a display device 220 capable of displaying a visual indicia, such as indicia 225 that may possess visual traits that may be used for visual testing and/or training purposes. Display device 220 may be positioned relative to subject 260 so that display device 220 may be perceived by subject 260 for visual testing and/or training purposes. Subject 260 may be a first distance 270 from display device 220. Input device 230 may comprise a joystick accessible by subject 260 for inputting based upon the perception of indicia 225 by subject 260. Alternatively, input device 230 may comprise a multi-touch device. Control unit 210 may connect to display device 220 via connection 252, and may connect to input device 230 via connection 254. System 200 illustrated in FIG. 2A is exemplary only, and other shapes, configurations, components, and combinations of components may be utilized in accordance with the present invention.

Figure 2B:
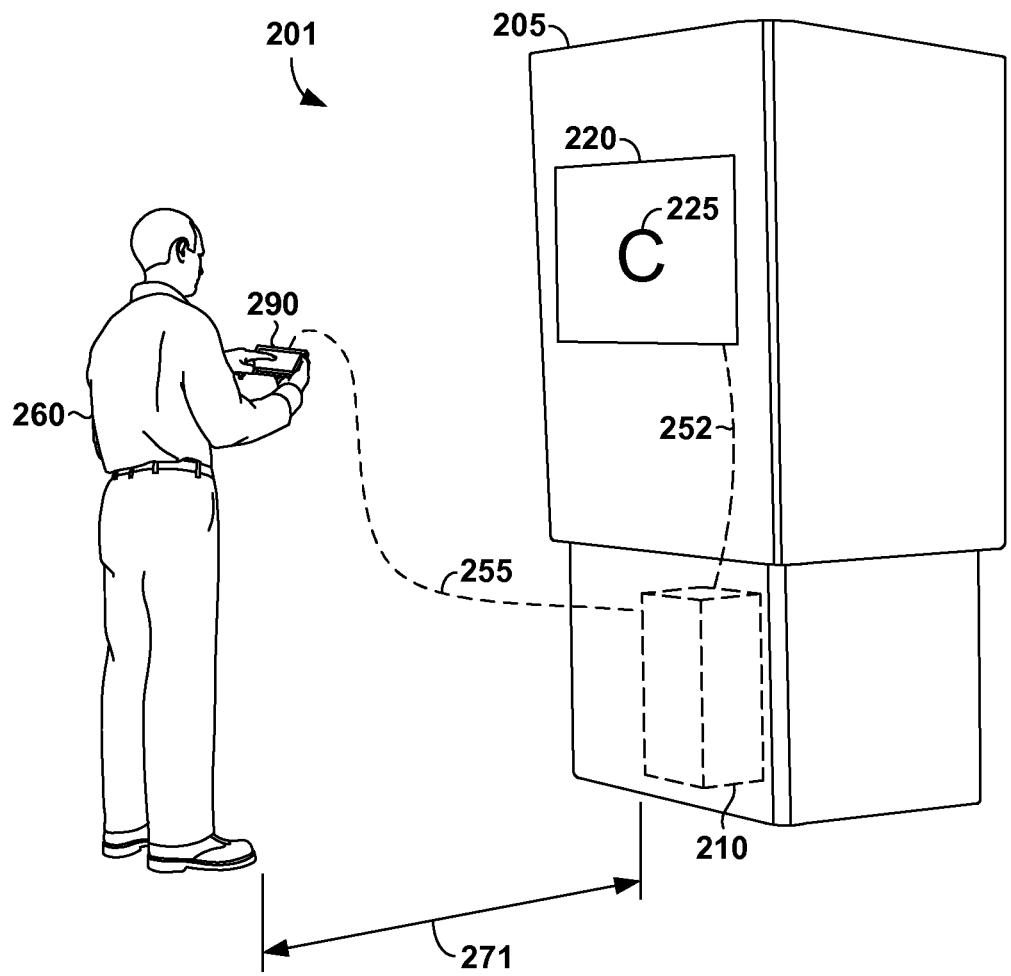

Referring now to FIG. 2B, an alternative example of a testing and/or training kiosk 205 in accordance with the present invention is illustrated. In the example illustrated in FIG. 2B, subject 260 utilizes a multi-touch device 290 as an input device. Multi-touch device 490 may be swiped in the direction of the orientation of a displayed indicia, such as indicia 225. Multi-touch device 390 may communicate wirelessly with control unit 210 via wireless link 255. Wireless link 255 may utilize any wireless protocol, including Bluetooth and/or various 802.11 protocols. In the example illustrated in FIG. 2B, subject 260 is located a second distance 271 from display device 220. Second distance 271 may be sufficient to approximate optical infinity for subject 260, but may be any distance. A distance of approximately 16 feet for second distance 271 may be useful for testing and/or training visual sensitivity.

Figure 3A:
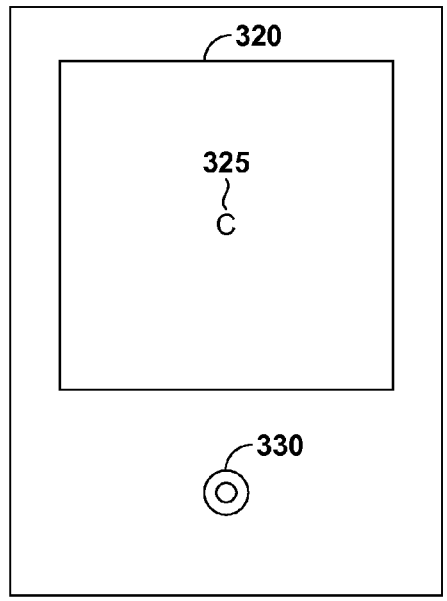
FIGS. 3A-3C illustrate the display of adaptable indicia in accordance with the present invention.
Figure 3B:
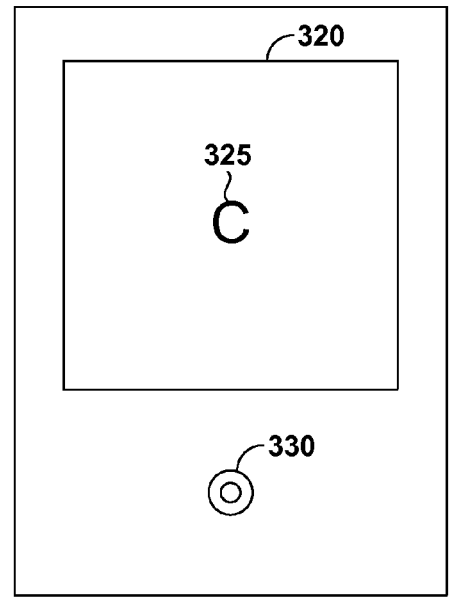
Figure 3C:
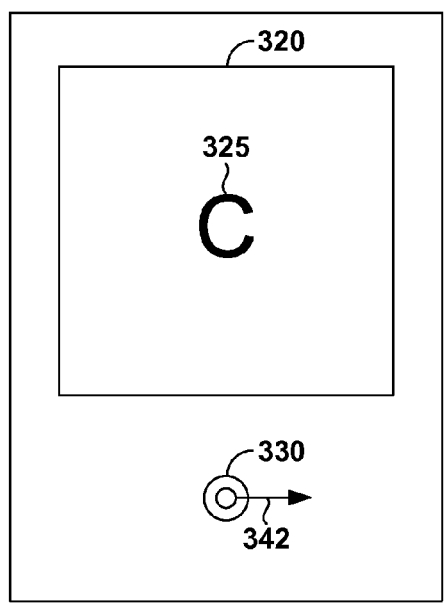

Referring now to FIGS. 3A-3C, an adaptable indicia 325 at different times in its display on display device 320 are illustrated. FIG. 3A illustrates indicia 325 at a first time. At the time illustrated in FIG. 3A, indicia 325 is displayed on display device 325 at a size too small to be perceived by subject (not shown) and, therefore, no input is entered using joystick 330. Indicia 325 at a second time is illustrated in FIG. 3B. At the time illustrated in FIG. 3B, indicia 325 remains at a size below that which may be perceived by subject (not shown), meaning that no input is registered on joystick 330 at the time illustrated in FIG. 3B. At the time illustrated in FIG. 3C, indicia 325 has increased in size so that subject (not shown) may perceive the visual trait possessed by indicia 325. In the example illustrated in FIGS. 3A-3C, indicia 325 comprises a Landolt C having an orientation to the right. Accordingly, when subject (not shown) perceives indicia 325 as being oriented to the right joystick 330 is depressed to the right as indicated by arrow 342 in FIG. 3C. By subject (not shown) manipulating joystick 330 to enter an input indicating the perceived orientation of indicia 325 whenever indicia 325 attains a size such that subject (not shown) may perceive indicia 325, the visual acuity of subject (not shown) may be assessed as part of visual testing and/or training.

Referring now to FIGS. 4A-4D, a plurality of indicia possessing different visual traits are illustrated in conjunction with an input device 430 capable of receiving a variety of inputs corresponding to the plurality of traits possessed by a displayed indicia. In the example illustrated in FIGS. 4A-4D the exemplary indicia illustrated are Landolt C's possessing the exemplary trait of one of four mutually exclusive orientations. Other types of indicia may be used in accordance with the present invention, and indicia may possess traits other than orientation. For example, indicia may be letters of the English alphabet that possess the trait of identity. Further, an indicia may possess a multitude of non-exclusive traits, such as identity and orientation. Of course, inputs corresponding to traits may be made in numerous fashions beyond the example of manipulating a joystick provided in FIGS. 4A-4D. For example, multi-touch devices, key boards, buttons, voice recognition, and the like may be used without departing from the present invention.

Figure 4A:
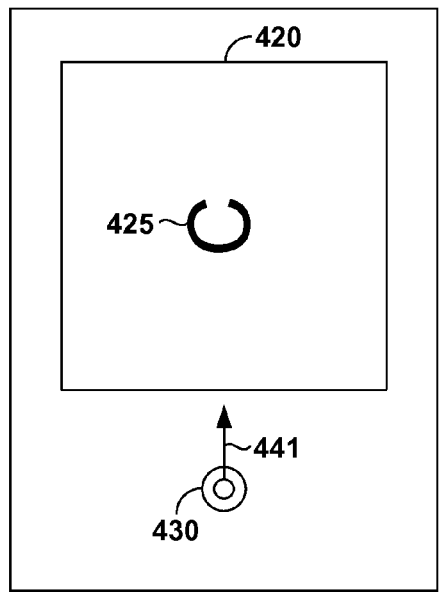
FIGS. 4A-4D illustrate the display of indicia in accordance with the present invention.

Referring now to FIG. 4A, a first indicia 425 comprises a Landolt C having an upward orientation displayed by display device 420. Joystick 430 may be manipulated in a corresponding direction 441 by subject (not shown) to indicate that subject (not shown) perceived first indicia 425 and perceived the visual trait possessed by first indicia 425.

Figure 4B:
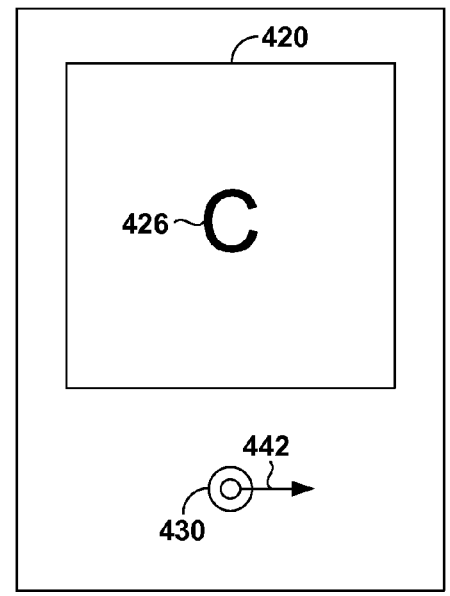

Referring now to FIG. 4B, a second indicia 426 may comprise a Landolt C having an orientation to the right displayed by display device 420. Joystick 430 may be manipulated in a corresponding direction 442 subject (not shown) perceived the second indicia 426 and perceived the visual trait possessed by second indicia 426.

Figure 4C:
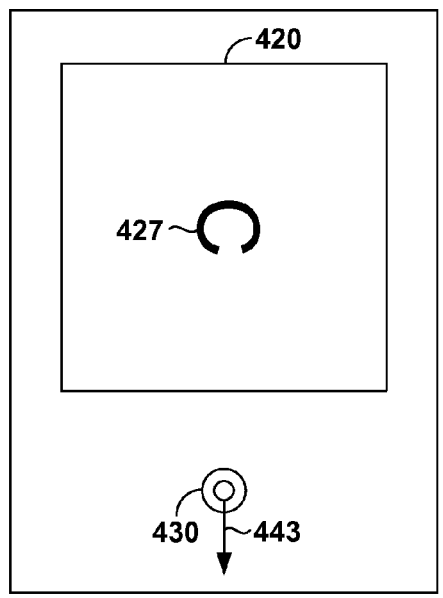

Referring now to FIG. 4C, a third indicia 427 may comprise a Landolt C possessing a downward orientation displayed by display device 420. Joystick 430 may be manipulated in a downwards direction 443 when subject (not shown) perceives the orientation of third indicia 427.

Figure 4D:
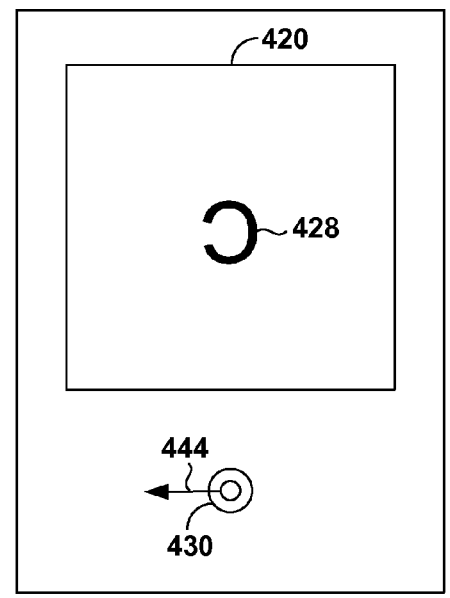

Referring now to FIG. 4D, a fourth indicia 428 may comprise a Landolt C having a leftward orientation displayed by display device 420. Joystick 430 may be manipulated in a corresponding direction 444 by subject (not shown) to indicate that subject (not shown) perceived fourth indicia 428 and perceived the visual trait possessed by fourth indicia 428.

Figure 5A:
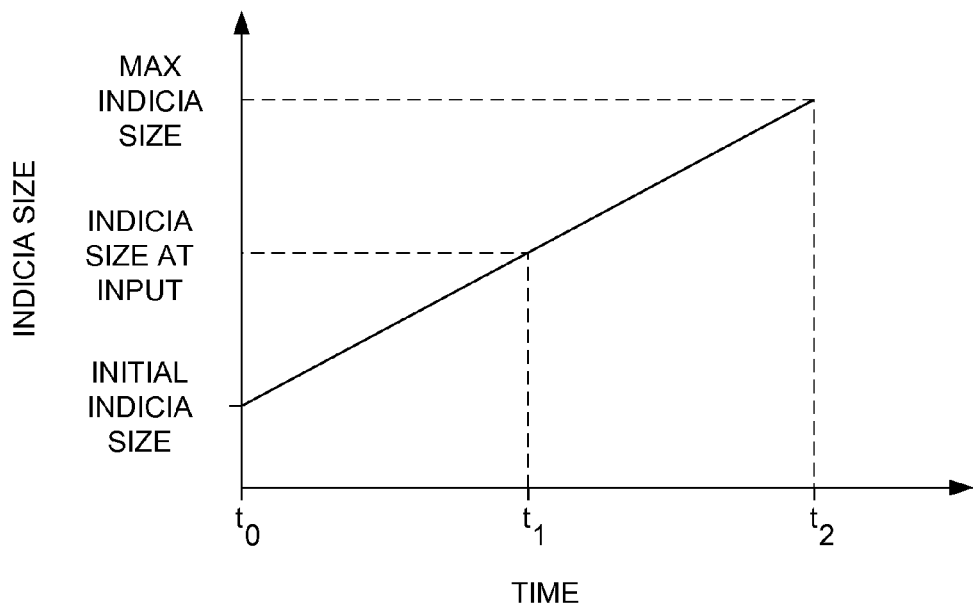
FIGS. 5A and 5B illustrate examples of the change in size of an adaptable indicia over time in accordance with the present invention.

Referring now to FIG. 5A, indicia size relative to time in an example of the changing indicia in accordance with the present invention is illustrated. In the example illustrated in FIG. 5A, the size of the indicia varies in a linear relationship with time. At a first time, "$t_1$", an indicia is displayed having an initial indicia size. The initial indicia size may be selected so as to be imperceptible to any individual to be tested. The indicia size may then grow at a substantially constant rate, such as the linear rate illustrated in FIG. 5A, until an input is received, for example, at time "$t_1$". At time "$t_1$" the indicia will possess a size. Both the time of input "$t_1$" and/or the size of indicia at input may be recorded and may be useful for assessing the visual acuity of an individual. At some point, such as, for example, time "$t_2$", an indicia will reach its maximum allowable size. The maximum allowable indicia size may be predetermined in the configuration of a visual sensitivity testing and/or training system. For example, there may be some point at which a given subject suffers from such serious deficiencies in visual acuity that no further increase in the size of a displayed indicia is warranted. Further, a given display device may limit or effectively limit the displayable size of an indicia. In either case, at some point an indicia may not be enlarged further, resulting in essentially a "timeout" scenario in a test methodology, which may result in the test being terminated, another indicia being displayed at an initial indicia size, an adjustment being made to the initial indicia size of a subsequently displayed indicia, or other measures being taken.

Figure 5B:
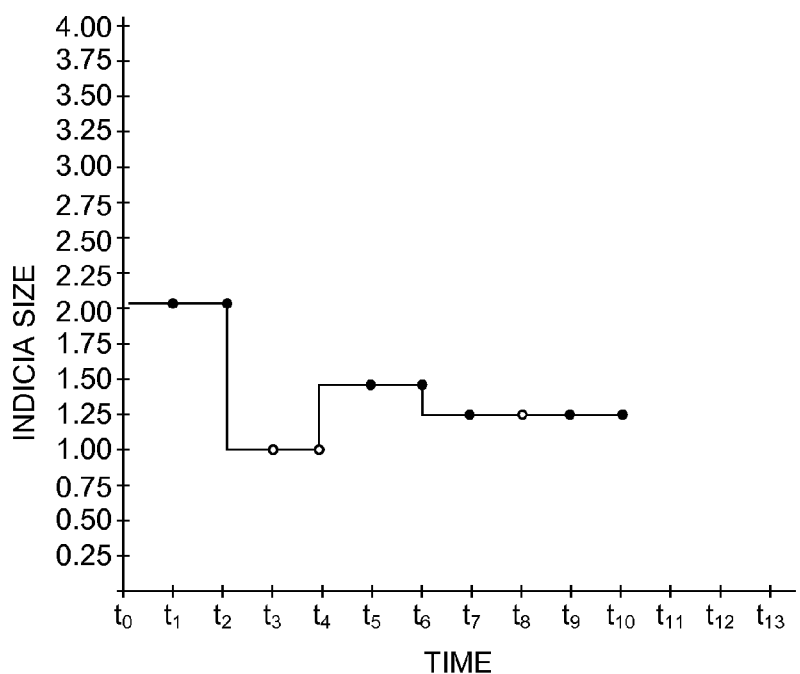

Referring now to FIG. 5B, indicia size relative to time in an example of the present invention that uses a step-wise indicia size adjustment is illustrated. In the example illustrated in FIG. 5B, an indicia may possess any of a plurality of specifically defined sizes, ranging in this example from a minimum of 0.25 to a maximum of 4.00 in increments of 0.25. A numerical description of the size of an indicia, such as the example illustrated in FIG. 5B, may refer to an absolute size (i.e., in inches, centimeters, etc.), an angular size in the field of view of a subject, or based on the number of pixels in size an indicia is on a display device. This size range is merely exemplary, however, and may be implemented using more or fewer discreet size levels. The possible indicia sizes may be selected based upon the distance a subject is to be positioned from a display device to provide an adequate range of visual sensitivity testing and/or training abilities. For example, there may be no need to assess or train the visual skills of an individual to better than a 0.25 level, so no indicia below that visual acuity level is necessary. Similarly, a particular embodiment of the present invention may not seek to test and/or train the visual acuity of a subject that is worse than 20/200. The specific size range of an indicia may be selected to provide adequate points of assessment between the minimum size needed and the maximum size needed. In the example illustrated in FIG. 5B, an indicia is initially displayed at time $t_0$ having a size of 2.00. The indicia will be displayed at that size for at least a predetermined period of time, during which subject (not shown) may respond. As indicated in FIG. 5B by the solid circle, that time $t_1$ the subject has provided a correct response. Thereafter, the indicia may be changed to possess a different trait while remaining at the same size. From time $t_1$ and time $t_2$ with indicia still at size 2.00, the subject has provided another correct response as is indicated by the solid circle. After two consecutive correct responses, the displayed indicia size may be decreased by an entire step to size to 1.00 at time $t_2$. Thereafter, as indicated by the empty circle at time $t_3$, subject (not shown) may provide an incorrect response or fail to provide any response to the displayed indicia. At time $t_3$, the displayed indicia may be changed to possess a different trait while remaining at size 1.00. In the example illustrated in FIG. 5B, subject (not shown) has incorrectly responded or failed to respond to that displayed indicia by time $t_4$. Thereafter, the displayed indicia is increased in size by half a step to a size 1.50 at time $t_4$. As indicated by the solid circle, by time $t_5$, the subject has provided a correct response. Thereafter, the displayed indicia is changed to possess another trait and is again displayed still at size 1.50. As indicated by the solid circle, subject (not shown) has responded correctly at time $t_6$. Thereafter, the displayed indicia may be decreased in size by a quarter step to size 1.25. As illustrated in the example of FIG. 5B, subject (not shown) provides a correct response at time $t_7$ and size 1.25, an incorrect or no response at time $t_8$ at size 1.25, and correct responses at size 1.25 at times $t_9$ and $t_{10}$. At this point, the example illustrated in FIG. 5B may conclude with the determination that the visual acuity of subject (not shown) may be concluded to presently be that which corresponds to a displayed indicia size of 1.25. Other types of stair step algorithms instead of or in addition to that illustrated in FIG. 5B may be used.

Figure 6A:
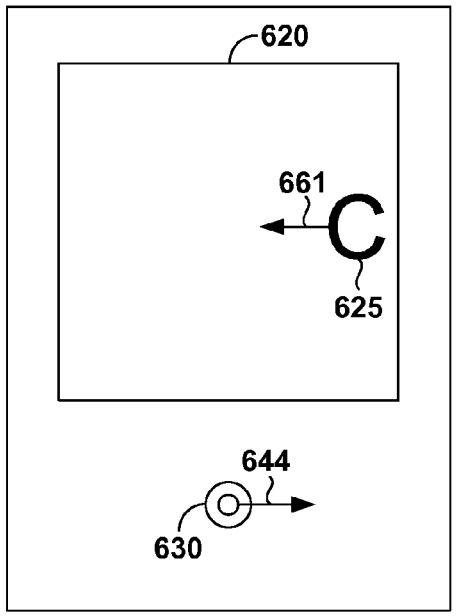
FIGS. 6A-6C illustrate an adaptable dynamic visual indicia in accordance with the present invention.
Figure 6B:
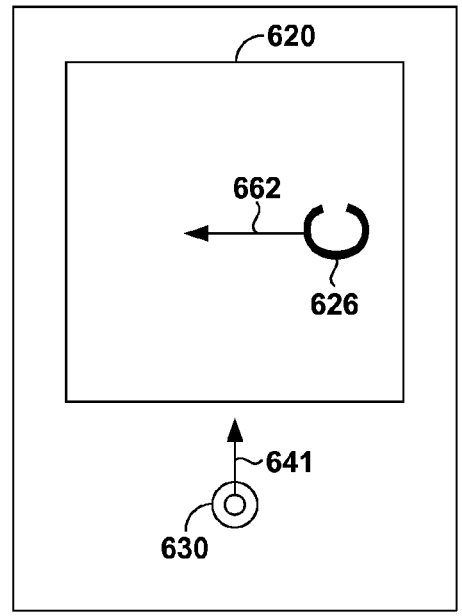
Figure 6C:
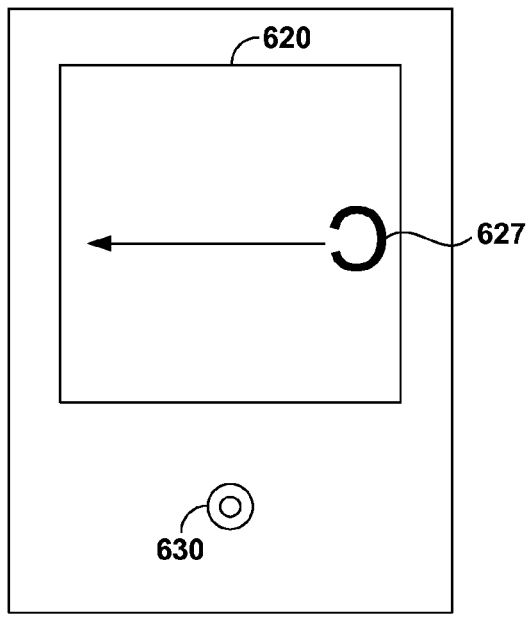
Figure 7A:
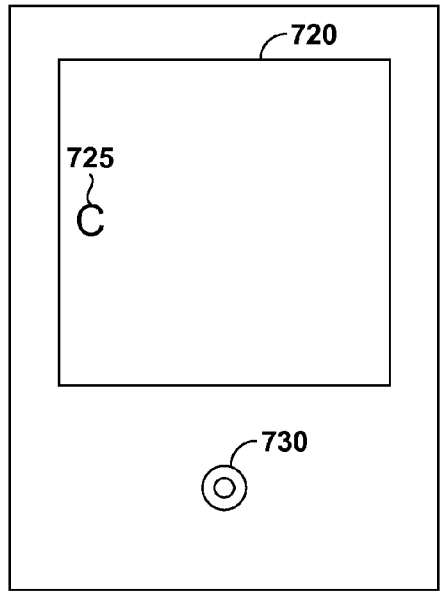
FIGS. 7A-7D illustrate an adaptable dynamic visual indicia in accordance with the present invention.
Figure 7B:
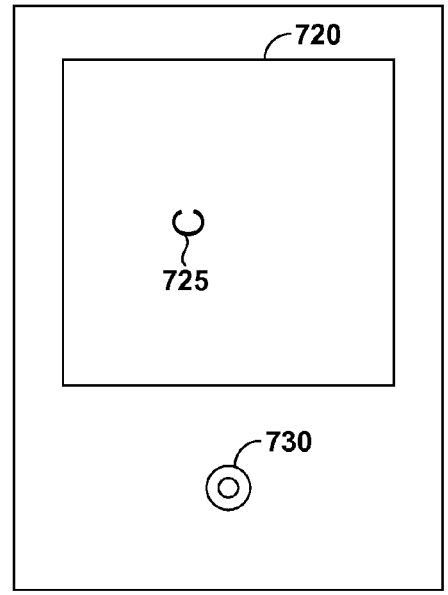
Figure 7C:
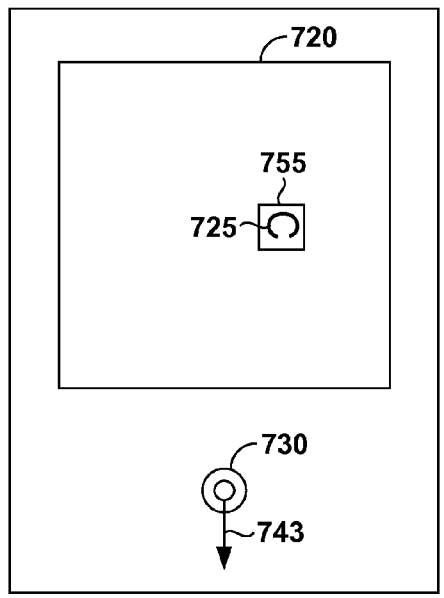
Figure 7D:
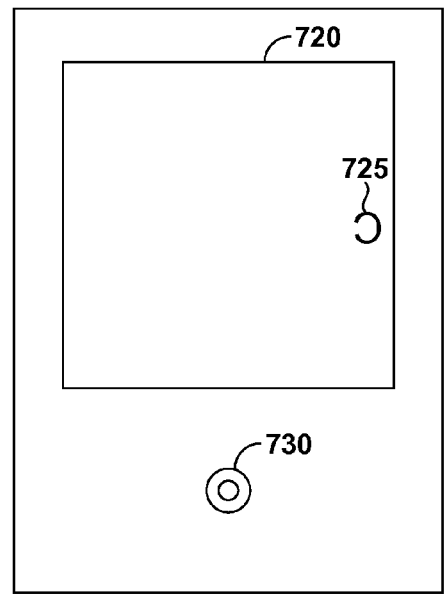
Figure 8A:
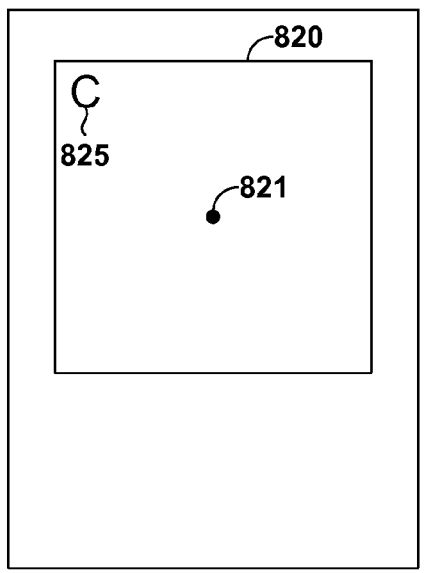
FIGS. 8A-8D illustrate an adaptable indicia used for testing and/or training target capture abilities in accordance with the present invention.
Figure 8B:
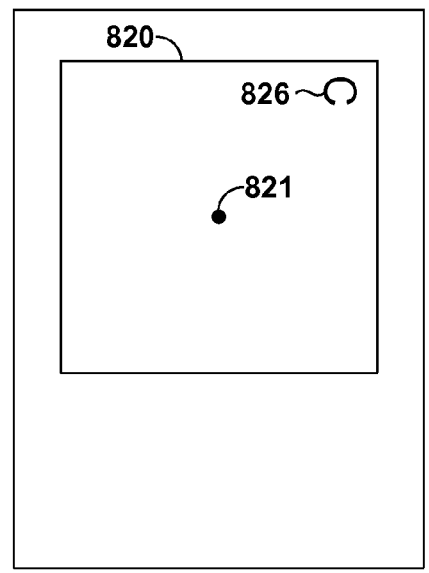
Figure 8C:
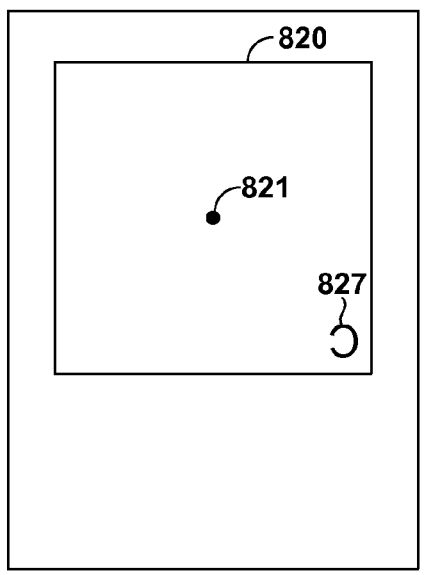
Figure 8D:
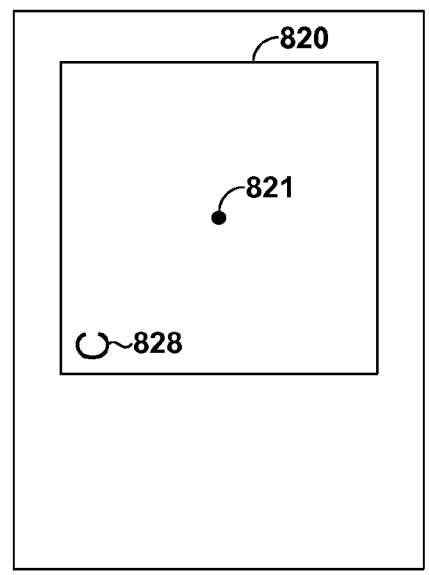

Referring now to FIGS. 6A-6C, an example of adaptable visual indicia for use in testing and/or training dynamic visual acuity is illustrated. Generally speaking, FIGS. 6A-6C illustrate a moving visual indicia possessing visual traits, at different trials with different trials using different rates of movement. In each trial, a subject (not shown) may attempt to perceive the moving visual indicia and the trait the indicia possesses subject (not shown) may provide an input corresponding to the visual trait perceived by subject (not shown), in these examples an orientation. As illustrated in FIGS. 6A-6C, iterations at varying indicia speeds may indicate at what speed an individual's dynamic visual acuity may no longer correctly perceive the visual trait of a displayed indicia. Further, the direction and/or angle of movement may vary in different iterations in order to determine, for example, the relative visual abilities of a subject for different types of movement. Further, the movement of an indicia need not be in a straight line and/or at a constant speed. In yet another exemplary embodiment, an irregular movement associated with and/or an unpredictable location at which the indicia travels may be employed. The inconsistencies introduced with irregular movements and/or unpredictable locations may prevent a subject from relying on saccadic movement during a testing and/or training activity. Additionally, it is contemplated that the presentation of an indicia may occur at any location and/or at any time within a testing and/or training activity.

In FIGS. 6A-6C the speed at which a given indicia is moving across a display device 620 is indicated by the length of the arrow associated with the indicia, while the direction of movement is indicated by the direction of the arrow. While the exemplary indicia displayed in FIGS. 6A-6C move from right to left across the display device, indicia in accordance with the present invention may move on a display device in any direction, including diagonally or at an other angle across a display device, and will further appreciate that within any given test indicia may move in more than one direction i.e., from right to left some iterations, from left to right in other iterations as well as up and down or diagonally. Further, one of skill in the art will appreciate that indicia beyond the illustrated example of Landolt C's may be used and that traits other than a directional orientation may be possessed by an indicia.

Referring now to FIG. 6A, a first indicia 625 on display device 620 may possess a visual trait, in this example a rightward orientation. First indicia 625 may move at a first speed 621. Subject (not shown) may indicate that first indicia 625 and the visual trait it possesses has been perceived by manipulating joystick 630 in a direction 644 corresponding to the trait possessed by first indicia 625.

Referring now to FIG. 6B, a second indicia 626 on display device 620 may possess a visual trait, in this example an upward orientation. Second indicia 626 may move at a second speed 662 which in the present example, exceeds first speed 621. Subject (not shown) may indicate that second indicia 626 and the visual trait if possesses has been perceived by manipulating joystick 630 in a direction 641 corresponding to the trait possessed by second indicia 626.

Referring now to FIG. 6C, a third indicia 627 on display device 620 may possess a visual trait, in this example a leftward orientation. Third indicia 627 may move at a third speed 663. As illustrated in FIGS. 6A-6C, third speed 663 exceeds first speed 661 substantially, and also exceeds second speed 662. Subject (not shown) cannot perceive the orientation of third indicia 627 in the present example and, accordingly, input was registered by manipulating joystick 630. Of course, a subject incorrectly perceiving the visual trait of a displayed indicia may, rather than not providing any input, provide an incorrect input. Further, on some occasions a subject may be incapable of perceiving the visual trait of a displayed indicia but will correctly guess at the visual trait possessed by an indicia and thereby provide the correct input. The issue of successful guessing may be addressed by using a sufficient number of iterations.

Referring now to FIGS. 7A-7D, an indicia 725 moving across a display device 720 is illustrated at different points in time. Indicia 725 in the example illustrated in FIGS. 7A-7D is a Landolt C possessing a trait of orientation, although other types of indicia and/or other traits possessed by indicia may be used without departing from the scope of the present invention. As further illustrated in the example of FIGS. 7A-7D, indicia 725 has a changing trait, in this case orientation, as it moves across the screen of display device 720. Indicia 725 may be described as a tumbling Landolt C, in that its orientation moves, or "tumbles" as it moves across display device 720. In the example illustrated in FIGS. 7A-7D, no input is required from a subject (not shown) using joystick 730 until a response is indicated by a second stimuli. In the present example, the secondary stimuli comprises a box 755 displayed around indicia 725. At a first time illustrated in FIG. 7A, indicia 725 is positioned near the left edge of display device 720 and possess a rightward orientation. At a second time illustrated in FIG. 7B, indicia 725 has moved to left of center of the display device 720 and possesses an upward orientation. At the point of time illustrated in FIG. 7C indicia 725 has moved to the right of center of display device 720 and possesses a downward orientation. At the point of time illustrated in FIG. 7C of this example, exemplary secondary stimuli, box 755, has been displayed around indicia 725, indicating to subject (not shown) to register an input if the subject perceives the trait possessed by indicia 725 which, in this example, is downward. Subject (not shown) may indicate that he or she has perceived the downward orientation trait possessed by indicia 725 by engaging joystick 730 in a corresponding movement 743. At the point in time in FIG. 7D, indicia 725 has progressed further to the right side of display device 720 and has an orientation of leftward. Other secondary stimuli may be used to indicate to a subject that he or she should enter an input beyond the use of display of box 755 as a secondary stimuli. For example, a sound, change of color, or any other stimuli may indicate to a subject that an input is to be made if the requisite visual trait of a displayed indicia may be perceived by the subject.

Referring now to FIG. 8A-8D, target capture testing and/or training using adaptable indicia are illustrated. In the example illustrated in FIGS. 8A-8D, a display device 820 displays a focal point 821 at or near the center of display device 820. A subject (not shown) may visually focus on focal point 821 and, at a time while subject is engaged in viewing focal point 821, an adaptable indicia may be displayed at some location of display device 820, such as a corner. However, an indicia may be displayed at any location on display device and, in fact, the location of a displayed indicia may be an adaptable characteristic in accordance with the present invention, i.e., training and/or testing may develop the target capture abilities of an individual at varying distances from focal point 821 and/or at different gaze angles on display device 820. Generally speaking, subject (not shown) focusing on focal point 821 will make a saccadic eye movement to visually acquire a displayed indicia and perceive a trait possessed by the indicia. In the examples illustrated in FIGS. 8A-8B, the indicia comprises a Landolt C possessing an orientation. The size of an indicia displayed for target capture testing and/or training may be based upon prior assessments of visual sensitivity determined using adaptable visual indicia as described herein, such as static visual acuity. Further, the examples illustrated in FIGS. 8A-8D utilize a multi-touch device 890 as an input device. Multi-touch device 890 may be swiped with a finger of subject (not shown) to indicate the direction of orientation of a displayed Landolt C. In the example illustrated in FIG. 8A, a first visual indicia 825 has appeared in the upper left corner of display device 820, and subject (not shown) has swiped multi-touch device 890 to the right as indicated by arrow 891. In the example illustrated in FIG. 8B, visual indicia 826 comprises a Landolt C appearing in the upper right hand corner of display device 820 and possessing a downward orientation, to which subject (not shown) responds by swiping multi-touch device 890 in a downward direction indicated by arrow 892. In the example illustrated in FIG. 8C, a visual indicia 827 has appeared in the lower right corner of display device 820 and comprises a Landolt C with a leftward orientation, to which subject (not shown) responds using multi-touch 890 by swiping to the left as indicated by arrow 893. In the example illustrated in FIG. 8D, the visual indicia 828 comprises a Landolt C in the lower left corner of display device 820 and possessing an upward orientation, to which subject (not shown) responds using multi-touch device 890 by swiping in an upward direction as indicated by arrow 894. In the examples illustrated in FIGS. 8A-8D, the displayed visual indicia 825, 826, 827, 828, may possess characteristics that vary in different iterations of testing and/or training. For example, the duration of time during which a given indicia is displayed may vary, the distance and/or direction of the displayed indicia from focal point 821 may vary, the color of an indicia may vary, the contrast of an indicia trait background may vary, the size of the indicia may vary, or any other visual characteristic of a displayed indicia either alone or in conjunction with its visual background may be varied.

Figure 9:
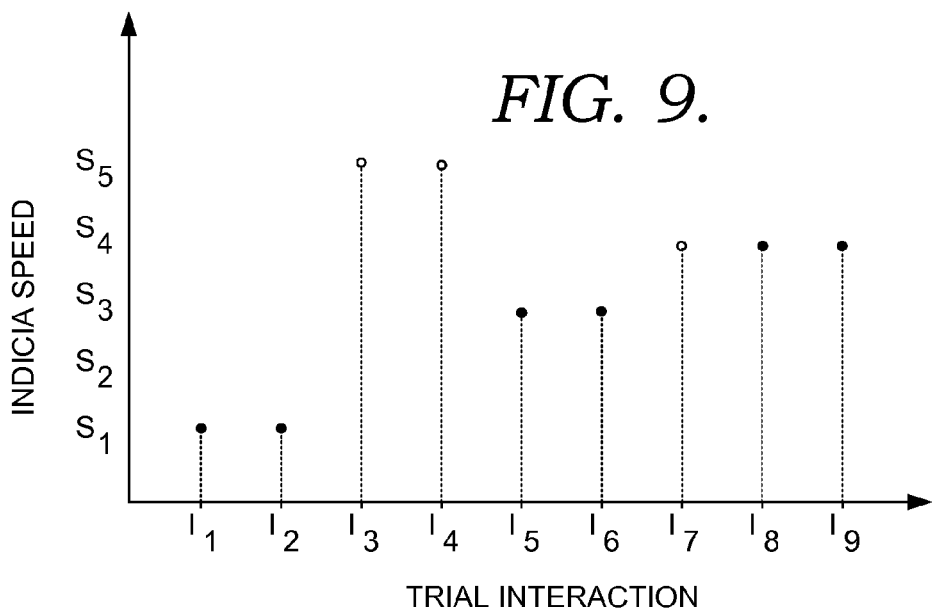
FIG. 9 illustrates the change in speed of a dynamic visual indicia over multiple iterations in accordance with the present invention.

Referring now to FIG. 9, indicia speed for different trial iterations, such as the trial iterations example illustrated in FIGS. 6A-6D, is illustrated. In FIG. 9, a solid dot indicates a correct input corresponding to a displayed indicia trait, while an open/empty dot/circle indicates either an incorrect response not corresponding to a displayed indicia trait or no response. In the example illustrated in FIG. 9, a plurality of trials are illustrated. In the example illustrated in FIG. 9, indicia moved at one of five speeds, denoted from slowest to fastest as $S_1, S_2, S_3, S_4,$ and $S_5$. In this example, trial iteration $I_1$ involved an indicia moving $S_1$ and, as indicated by the solid dot, a subject provided a correct input in response to the displayed indicia. As further illustrated in the example of FIG. 9, a second iteration denoted $I_2$ involved an indicia moving at the first speed denoted $S_1$. Iteration $I_2$ resulted in a correct response from subject, as denoted by the solid dot. In the example of FIG. 9, iteration $I_3$ occurred at speed $S_5$ and resulted in either an incorrect response from subject or no response from subject, as indicated by the open dot. In the example illustrated in FIG. 9, iteration $I_4$ occurred at speed $S_5$, which also resulted in either an incorrect response from subject or no response from subject, as indicated by the open dot. Thereafter in this example, subject provided an accurate response to iteration $I_5$ and $I_6$ at a speed $S_3$, an incorrect or no response for iteration $I_7$ at speed $S_4$, and two consecutive correct responses to iteration $I_8$ and $I_9$ at speed $S_4$. The dynamic visual acuity test illustrated as an example in FIG. 9 could proceed further after iteration $I_9$, but could also be determined to be concluded, with the dynamic visual acuity of a subject being measured as capable of resolving traits of indicia move at speed $S_4$.

Figure 10:
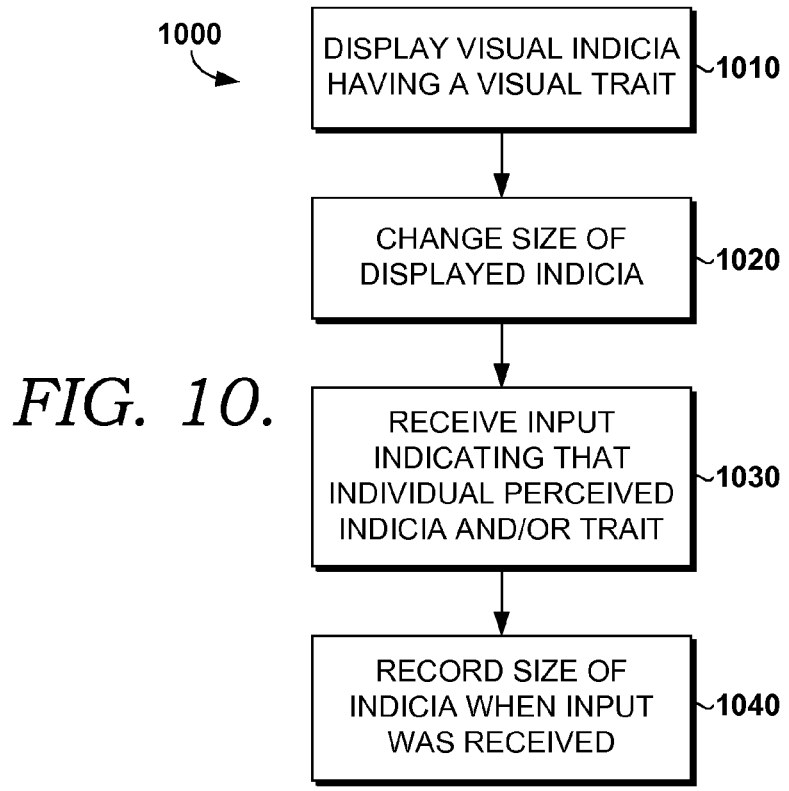
FIG. 10 illustrates a method in accordance with the present invention for testing and/or training static visual acuity.

Referring now to FIG. 10, a method 1000 for testing and/or training static visual acuity in accordance with the present invention is illustrated. In step 1010 a visual indicia having a visual trait may be displayed on a display device viewable by the subject. In step 1020 the size of the displayed indicia may be changed. For example, in step 1020 the displayed visual indicia may be increased in size. In step 1030 an input may be received from the subject indicating that the subject perceived the displayed indicia and/or the trait of the displayed indicia. The input may correspond to the trait possessed by the displayed indicia. In step 1040 the size of the indicia when the input was received may be recorded. Step 1010 may utilize a display device of any type, step 1030 may utilize any type of input device, and step 1040 may utilize any type of storage device. The performance of the steps of method 1000, and the additional methods described herein, may be controlled, directed, or monitored by one or more control units, as described herein.

Figure 11:
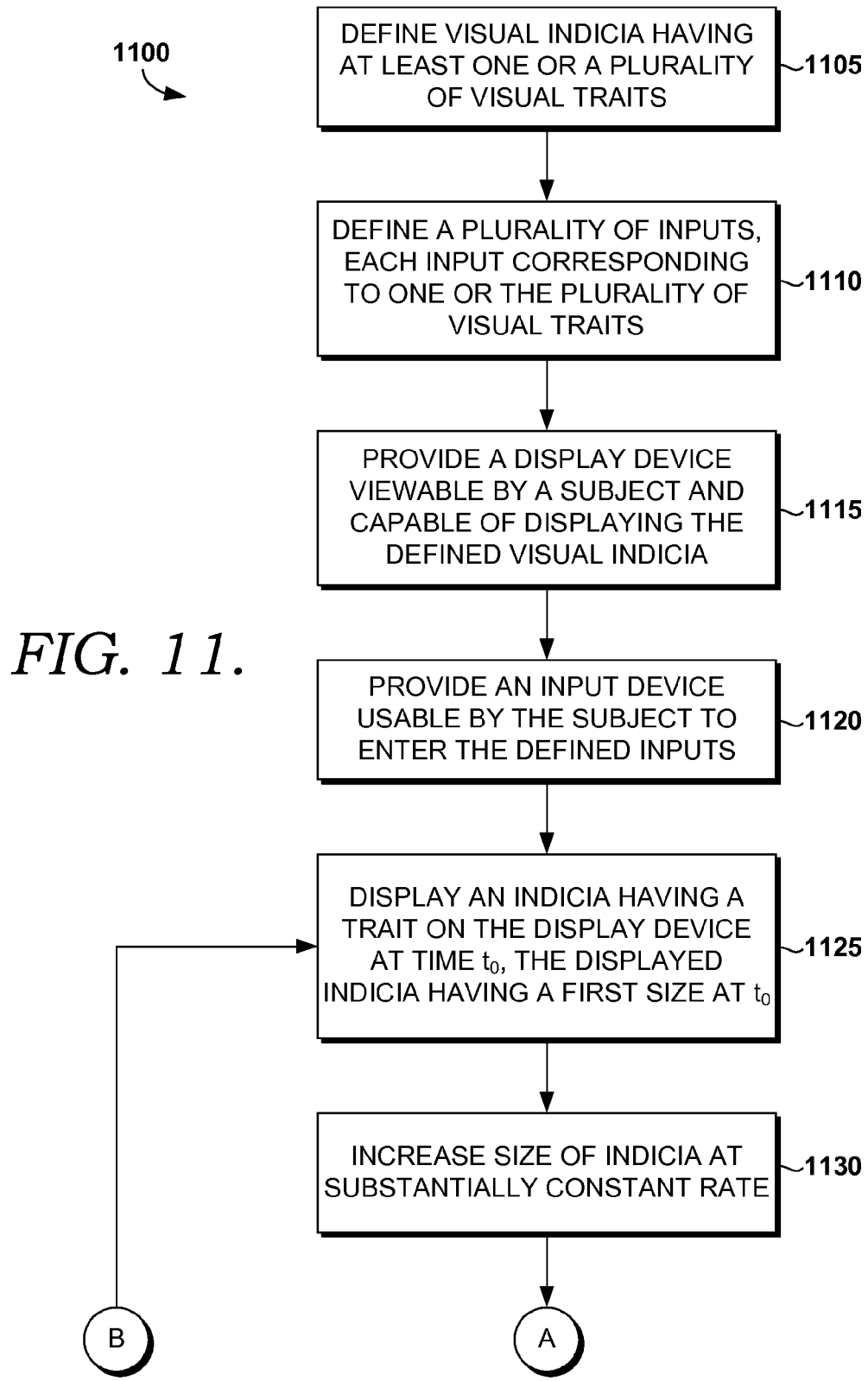
FIG. 11 illustrates a further method in accordance with the present invention for testing and/or training static visual acuity.
Figure 11:
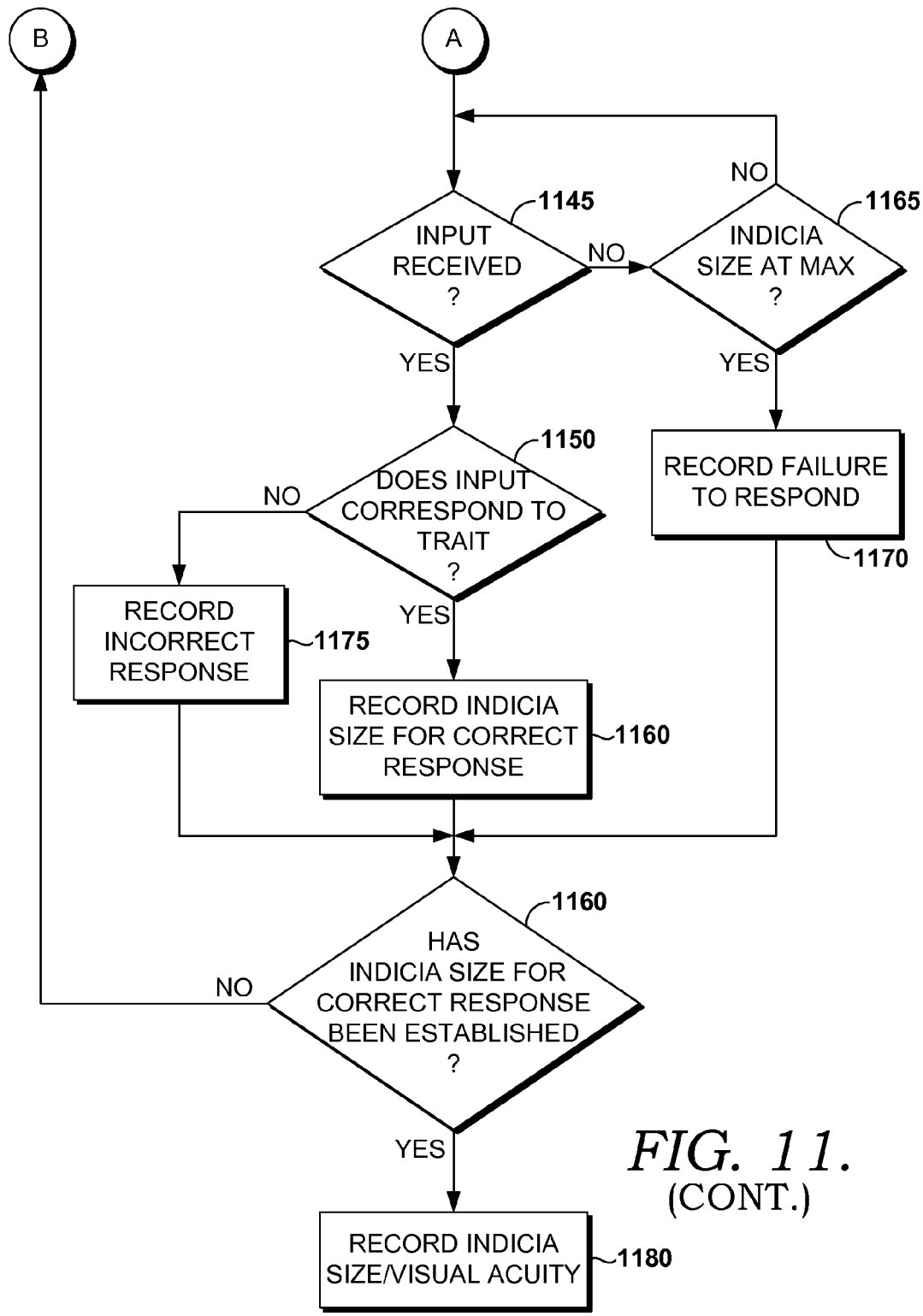

Referring now to FIG. 11, a further method 1100 in accordance with the present invention is illustrated. In step 1105, a visual indicia that may possess at least one of a plurality of visual traits may be defined. In step 1110 a plurality of inputs, each input corresponding to one of the plurality of visual traits may be defined. The inputs defined in step 1110 may correspond in a one to one fashion with the visual traits defined in step 1105. For example, step 1105 may define as visual indicia Landolt Cs having a plurality of visual traits, namely an orientation of upward, downward, leftward, or rightward. Similarly in this example, step 1110 may define a plurality of inputs, each input being a movement of the joystick up, down, left, or right in correspondence with a similar orientation of a displayed Landolt C. In step 1115 a display device may be provided to a subject such that the display device is viewable by the subject and capable of displaying the defined visual indicia. In step 1120 an input device may be provided to the subject that may be used to enter the defined inputs. Step 1120 may provide an input device capable of receiving inputs beyond those defined in step 1110. In step 1125 an indicia may be displayed on the display device having a trait at a time $t_0$, the displayed indicia having a first size at time $t_0$. In step 1130 the size of the displayed indicia may be increased at a substantially constant rate. The substantially constant rate of step 1130 may be linear or a constant stair-step. In step 1145 it is determined whether an input from the input device has been received. If no input has been received, method 1100 proceeds to step 1065 to determine whether the indicia has reached its size maximum. If the conclusion of step 1165 is that the indicia has not yet reached its size maximum method 1100 returns to step 1145 to determine whether an input has been received. If the conclusion of step 1165 is that the indicia has reached the size maximum, method 1100 proceeds to step 1170 of recording a failure to respond. If the conclusion of step 1145 as to whether an input has been received is yes, method 1100 proceeds to step 1150 to determine whether the input received corresponds to the trait of the displayed indicia. If the conclusion of step 1150 is that the input does not correspond to the trait of the displayed indicia, method 1100 proceeds to step 1175 to record an incorrect response. If the conclusion of step 1150 is to determine that the input does correspond to the trait of the displayed indicia, method 1100 proceeds to step 1155 to record the indicia size for the correct response and, optionally, that the response was correct and/or the trait possessed by the indicia. From any of steps 1155, 1170, and steps 1175, method 1100 may proceed to step 1160 to determine whether the indicia size for correct responses has been established. Step 1160 may determine, for example, that the responses of the subject permit a determination of the static visual acuity of the subject. If the determination of step 1160 is that the indicia size for correct responses has not been established method 1100 may return to step 1125 to display another indicia. If the conclusion of step 1160 is that the indicia size for correct responses has been established method 1100 may proceed to step 1180 of recording the indicia size/visual acuity measured for the subject.

Figure 12:
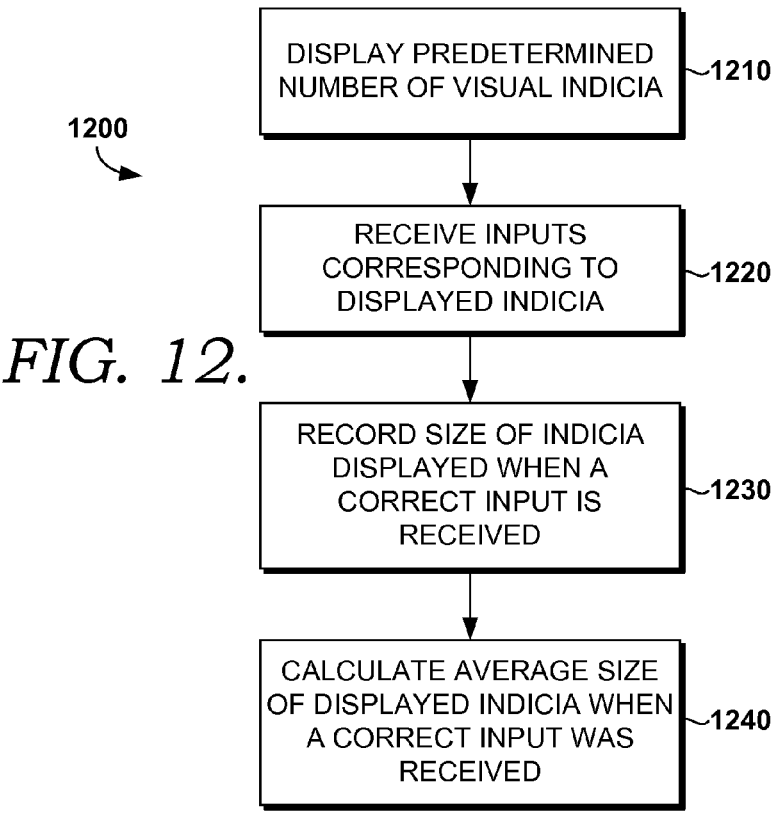
FIG. 12 illustrates a method in accordance with the present invention for testing and/or training the static visual ability of a subject.

Referring now to FIG. 12, a method 1200 for assessing whether the size of a perceptible indicia has been established is illustrated. In step 1210 a predetermined number of visual indicia are displayed. For example, the predetermined number of visual indicia may constitute ten indicia, which, as described further, may be used to attain an average size at which a subject provides a correct response. In step 1220 inputs may be received corresponding to each displayed indicia. In step 1230 the size of indicia displayed when a correct input is received may be recorded. In step 1240 the average size of displayed indicia when a correct input was received may be calculated. In this fashion, steps such as step 1160 of FIG. 11 may constitute simply averaging the size at which a correct response is received for a predetermined number of visual indicia.

Figure 13:
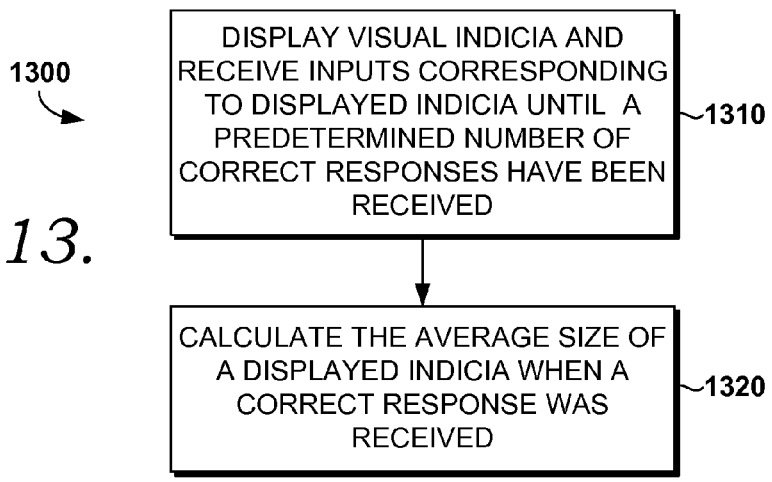
FIG. 13 illustrates a further method in accordance with the present invention for testing and/or training the static visual acuity of an individual.

Referring now to FIG. 13, a further method 1300 for assessing whether the size of a perceptible indicia has been established is illustrated. In step 1310 visual indicia may be displayed and inputs corresponding to the displayed indicia may be received until a predetermined number of correct responses have been received. For example, the display of indicia and the receipt of inputs may continue until a subject has provided ten correct responses. In step 1320 the average size of a displayed indicia when a correct response was received may be calculated. Similarly to method 1200, method 1300 may be utilized to determine at what size of indicia a subject may correctly perceive the indicia and/or its displayed traits. Unlike method 1200, method 1300 requires a predetermined number of correct responses, rather than a predetermined number of trials regardless of the correctness of the response.

Figure 14:
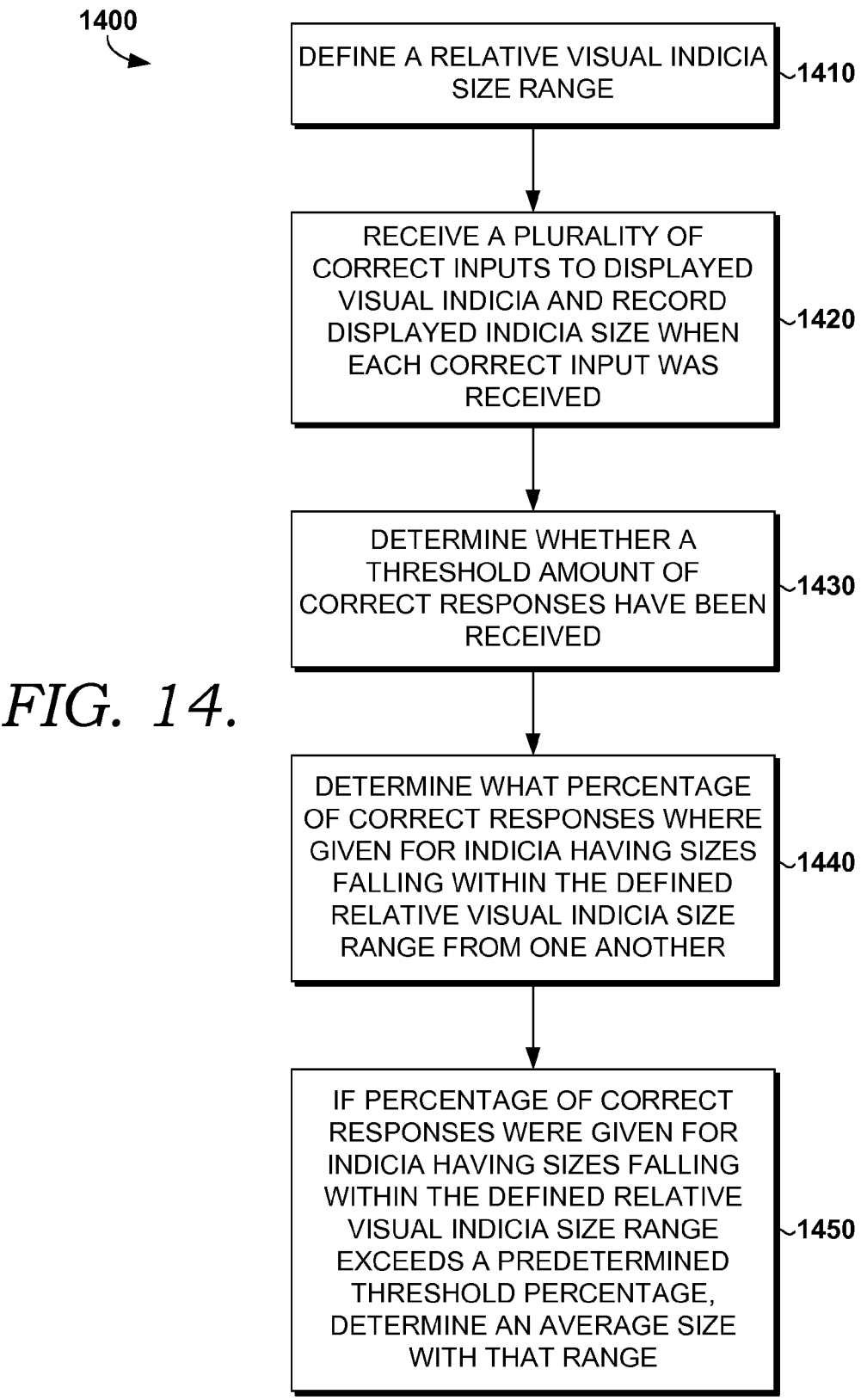
FIG. 14 illustrates a further method in accordance with the present invention for testing and/or training the static visual acuity of an individual.

Referring now to FIG. 14, a method 1400 for assessing the size of a perceptible indicia has been established is illustrated. In step 1410 a relative visual indicia size range may be defined. The size range defined in step 1410 may be absolute, such as an absolute size range of plus or minus two centimeters when displayed on a given display device. The size range defined in step 1310 may, alternatively, be relative, such as within ten percent of the diameter of a displayed indicia. In step 1420 a plurality of inputs correctly corresponding to displayed visual indicia may be received and the displayed indicia size may be recorded for each correct input. In step 1430 a determination may be made as to whether a threshold amount of correct responses have been received. In step 1440 a determination may be made as to what percentage of correct responses were given for indicia having sizes falling within the defined relative visual indicia size range from one another. In step 1450 if the percentage of correct responses to indicia having sizes falling within the defined relative visual indicia size range of step 1410 exceeds a predetermined threshold percentage, such as, for example, eighty percent, it may be determined that an average size within that range corresponds to the static visual acuity of the individual.

Figure 15:
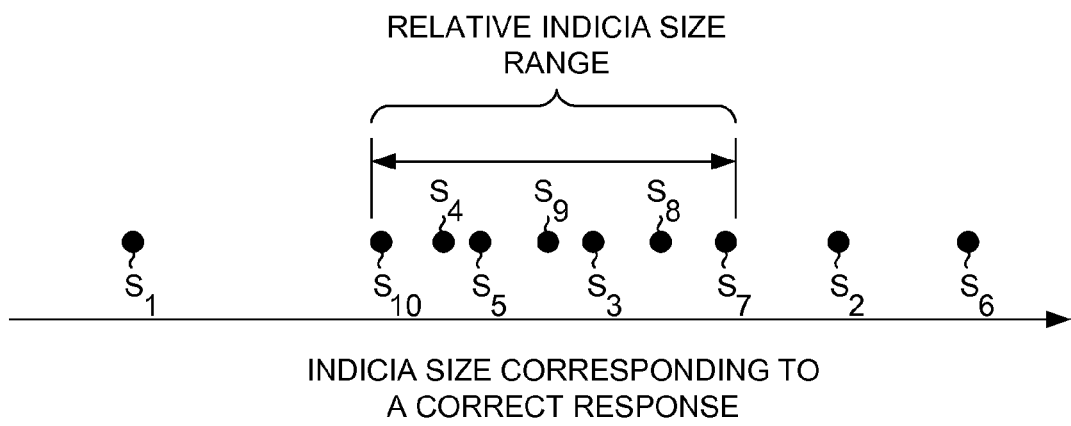
FIG. 15 illustrates an exemplary relative indicia size range attainable in testing and/or training static visual acuity in accordance with the present invention.

Referring now to FIG. 15, a defined relative indicia size range and test and/or training result are illustrated. In the example shown in FIG. 15, ten indicia sizes, denoted $S_1$ through $S_{10}$, are illustrated. Further, a relative indicia size range is shown graphically. Each size of indicia $S_1$-$S_{10}$ corresponds to a correct input from a subject. As illustrated in the example of FIG. 15, seventy percent, namely seven out of ten, of the correct responses were at an indicia size within the defined relative indicia size range. If the predetermined percentage threshold of step 1450 in method 1400 were seventy percent, then the receipt of a tenth correct input at size $S_{10}$ would permit the conclusion of testing with the calculation of the average of indicia sizes falling within the relative indicia size range as a measure of the static visual acuity of the individual. In the example illustrated in FIG. 15, the sizes of indicia corresponding to correct responses were sizes $S_3$, $S_4$, $S_5$, $S_8$, $S_9$, and $S_{10}$.

Figure 16:
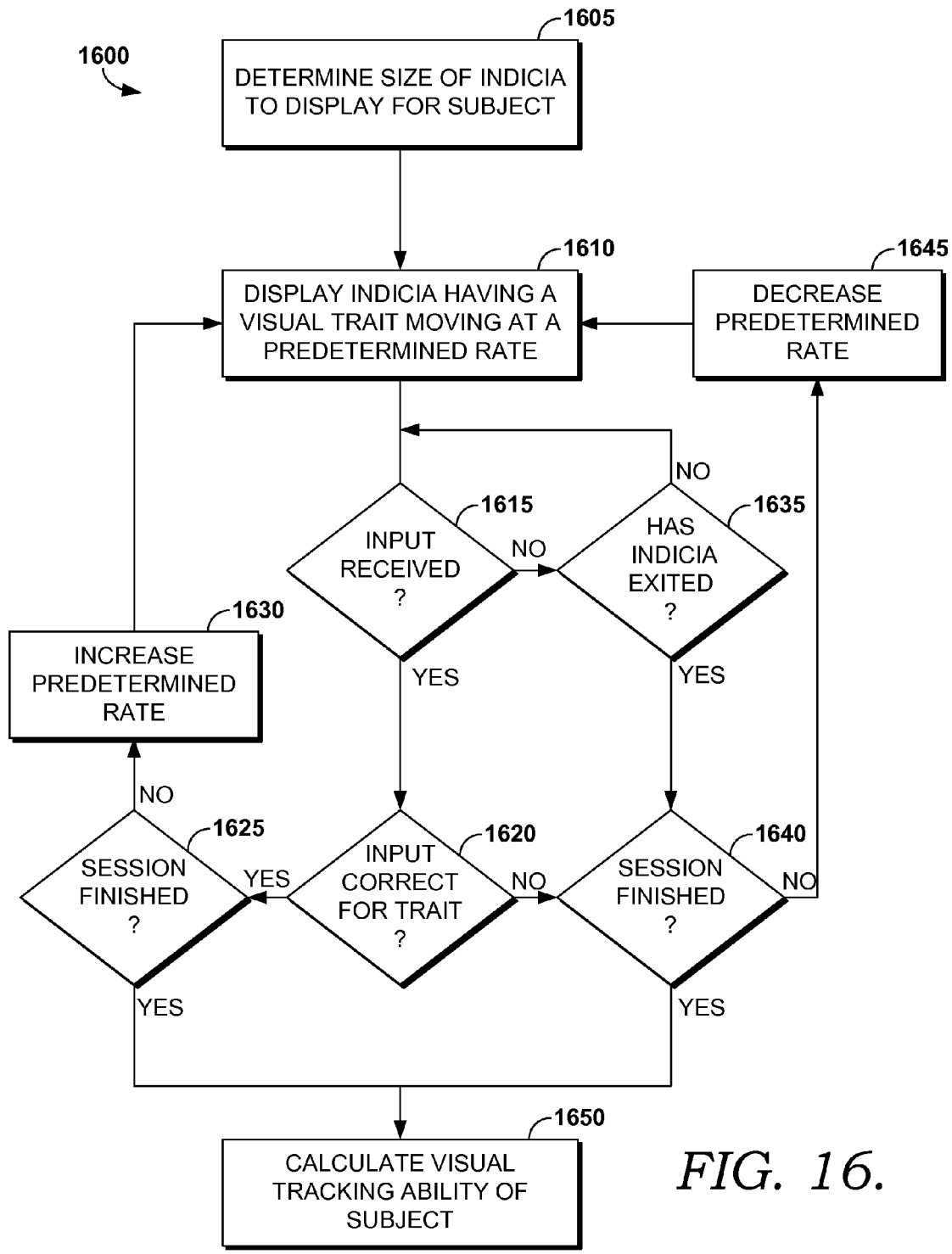
FIG. 16 illustrates a method in accordance with the present invention for testing and/or training the dynamic visual acuity of an individual.

Referring now to FIG. 16, a method 1600 for testing and/or training dynamic visual acuity of a subject is illustrated. In step 1605 the size of indicia to display for subject is determined. Step 1605 may utilize any of the methods for testing static visual acuity described herein, or may utilize other methods of measuring static visual acuity, such as conventional eye chart tests. In step 1610 an indicia having a visual trait moving at a predetermined rate is displayed. In step 1655 it is determined whether an input has been received. If the conclusion of step 1615 is that no input has been received, method 1600 may proceed to step 1635 to determine whether the indicia has exited the effective display area. If the conclusion of step 1635 is that the indicia has not exited, method 1600 may return to step 1615 to determine whether an input has been received. If the conclusion of step 1635 is that the indicia has exited the effective display area method 1600 may proceed to step 1640, which shall be discussed subsequently. If the conclusion of step 1615 is that an input has been received, method 1600 may proceed to step 1620 to determine whether the received input corresponded correctly to the trait of the displayed indicia. If the conclusion was that the input was not correct, method 1600 may proceed to step 1640 to determine whether the test is finished. If the conclusion of step 1640 is that the test is not finished, method 1600 may proceed to step 1645 to decrease the predetermined rate at which an indicia moves, and may thereafter return to step 1610 of displaying an indicia having a visual trait moving at a predetermined rate, now decreased in step 1645. If the conclusion of step 1620 is that a correct response was received, method 1600 may proceed to step 1625 to determine whether the test is finished. If the conclusion of step 1625 is that the test is not finished, method 1600 may proceed to step 1630 to increase the predetermined rate. Method 1600 may thereafter proceed to return to step 1610 to display an indicia having a visual trait moving at a predetermined rate, this time utilizing the predetermined rate increased in step 1630. If the conclusion of either step 1625 or step 1640 is that the test has finished, method 1600 may proceed to step 1650 of calculating the visual tracking ability of the subject. Step 1650 may provide a measure of the dynamic visual acuity of a subject.

Figure 17:
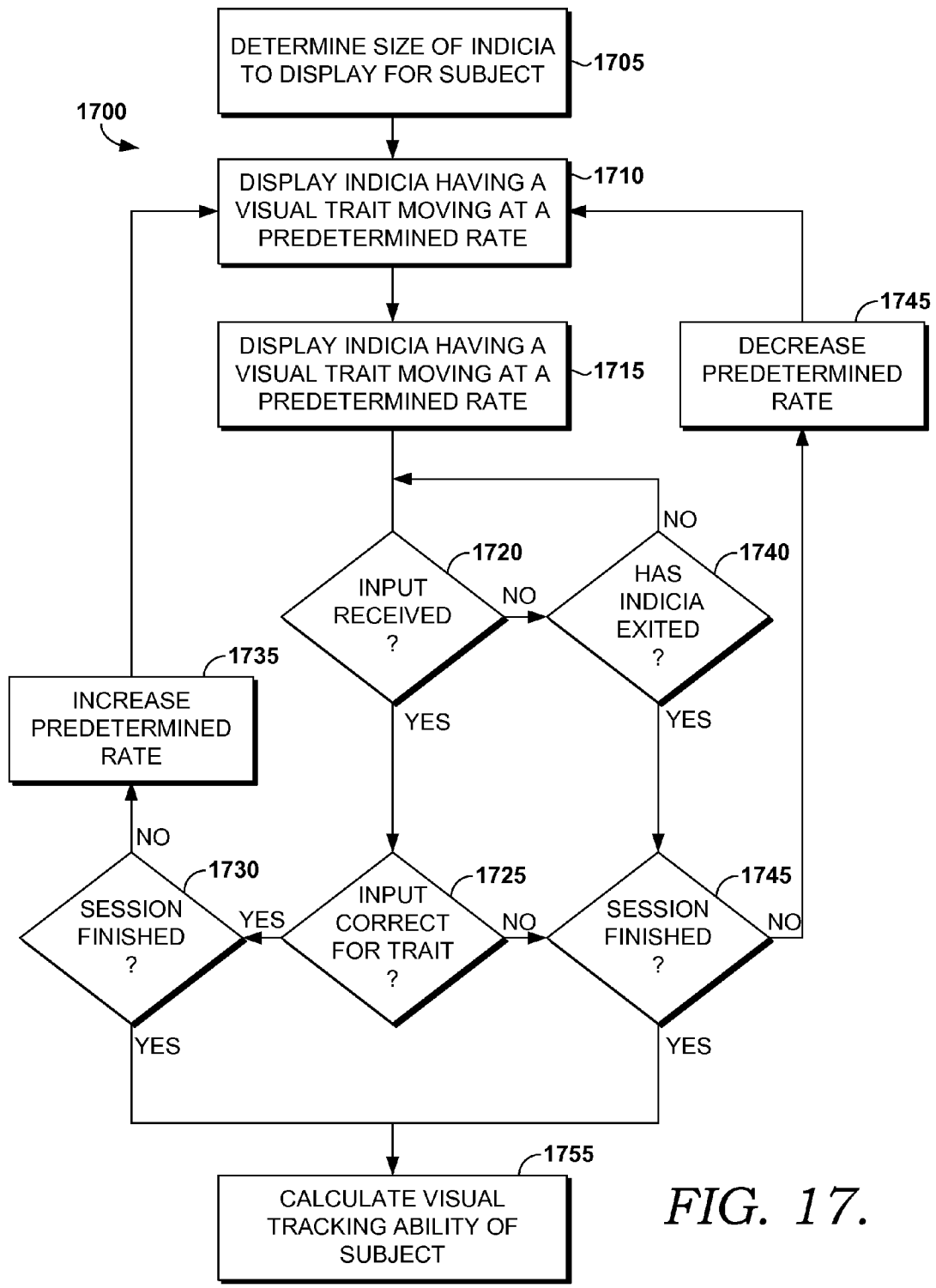
FIG. 17 illustrates a method in accordance with the present invention for testing and/or training the dynamic visual acuity of an individual.

Referring now to FIG. 17, a further method 1700 of testing and/or training the dynamic visual acuity of the subject is illustrated. In step 1705 the size of indicia to display for a subject may be determined. Step 1705 may utilize any of the static visual acuity testing and/or training methods described above, or may use any other method of testing and/or training static visual acuity, such as traditional eye chart tests. In step 1710 an indicia having a changing visual trait may be displayed moving at a predetermined rate. In step 1715 a secondary stimulus may be provided to the subject as a prompt to observe the visual trait of the indicia and to provide a corresponding input. The secondary stimulus provided as a prompt in step 1715 may be visual, such as displaying a box around the changing visual indicia, may be auditory, or may utilize other senses of a subject. Method 1700 may then proceed to step 1720 to determine whether an input has been received. If the conclusion of step 1720 is that no input has been received, method 1700 may proceed to step 1740 to determine whether the response time has elapsed. Response time may be defined, for example, by the duration of the prompt issued in step 1715, but may utilize other timeframes, such as whether a moving indicia has exited the display device. If the conclusion of step 1740 is that the response time has not elapsed, method 1700 may return to step 1720 to determine whether an input has been received. If the conclusion of step 1740 is that the response time has not elapsed, method 1700 may proceed to step 1745 to determine whether the test has finished. Step 1745 shall be addressed further below. If the result of step 1720 is that an input has been received, method 1700 may proceed to step 1725 to determine whether the input received correctly corresponded to the trait of the indicia displayed during the period of time for a response. If the conclusion of step 1725 is that the input received did not correctly correspond to the trait of the indicia, method 1700 may proceed to step 1745 to determine whether the test and/or training session has finished. If the conclusion of step 1745 is that the test has not finished, method 1700 may return to step 1750 to decrease the predetermined rate. Thereafter, method 1700 may return to step 1710 of displaying an indicia moving at a predetermined rate, now using the predetermined rate decreased in step 1750. If the result of step 1725 is that a correct response was received, method 1700 may proceed to step 1730 to determine whether the test has finished. If the conclusion of step 1730 is that the test and/or training session was not finished, method 1700 may proceed to step 1735 to increase the predetermined rate. Thereafter, method 1700 may return to step 1710 of displaying an indicia having a visual trait moving at a predetermined rate, this time utilizing the predetermined rate increased in step 1735. If the conclusion of either step 1730 or the conclusion of step 1745 is that the test is finished, method 1700 may proceed to step 1755 of calculating the visual tracking ability of the subject, which may comprise quantifying the dynamic visual acuity of the subject.

Figure 18:
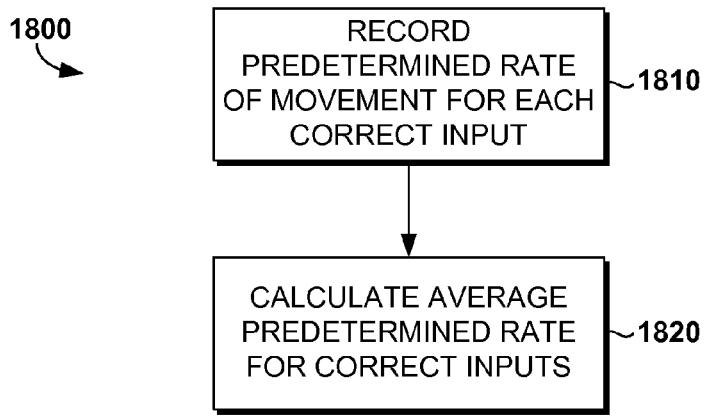
FIG. 18 illustrates a further method in accordance with the present invention for testing and/or training the dynamic visual acuity of an individual.

Referring now to FIG. 18, a method 1800 for testing and/or training the dynamic visual acuity of a subject is illustrated. In step 1810 the predetermined rate of movement for each correct input may be recorded. In step 1820 the average predetermined rate of movement for all of the correct inputs may be calculated. Method 1800 may be used in conjunction with any of the methods described herein for testing and/or training the dynamic visual acuity of a subject.

Figure 19:
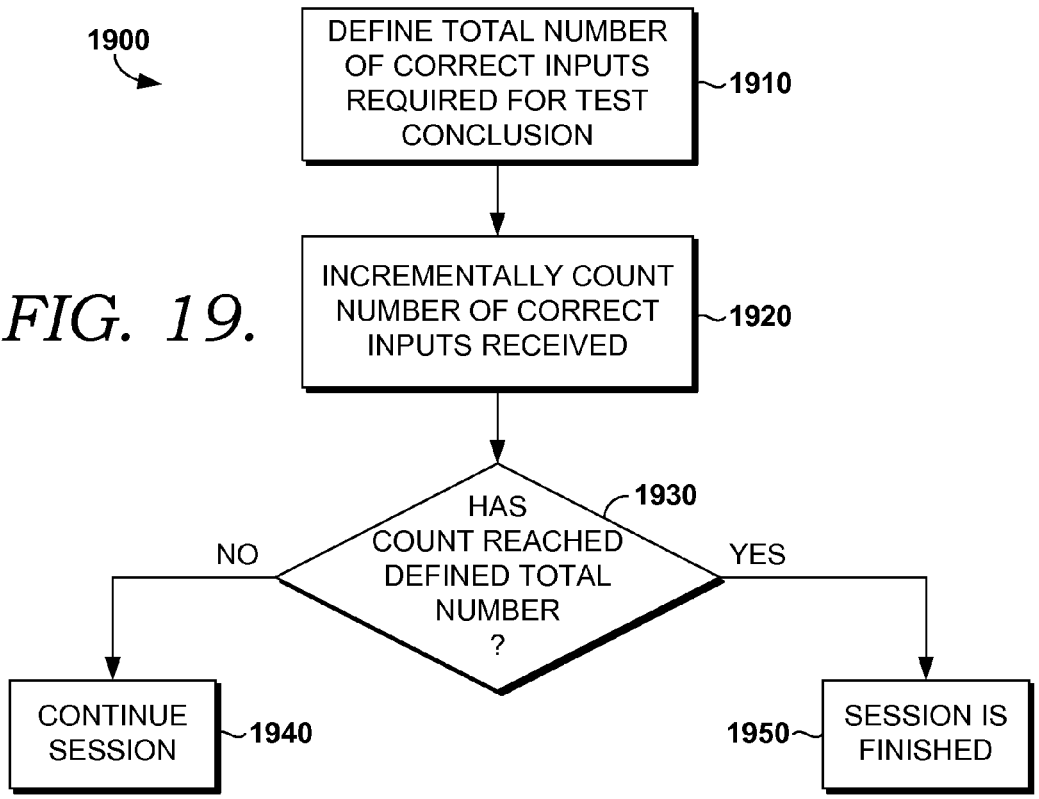
FIG. 19 illustrates a further method in accordance with the present invention for testing and/or training the dynamic visual acuity of an individual.

Referring now to FIG. 19, a further method 1900 for testing and/or training the dynamic visual acuity of a subject is illustrated. In step 1910 a total number of correct inputs required for test and/or training session conclusion may be defined. In step 1920 an incremental count may be kept of the number of correct inputs received. In step 1930, method 1900 may proceed to determine whether the count of correct responses has reached the total number of correct inputs defined in step 1910. If the conclusion of step 1930 is that the count has not reached the defined total number, method 1900 may proceed to step 1940 of continuing the test and/or training session. If the conclusion of step 1930 is that the count has reached the total defined number, method 1900 may proceed to step 1950 and determine that the test and/or training has concluded.

Figure 20:
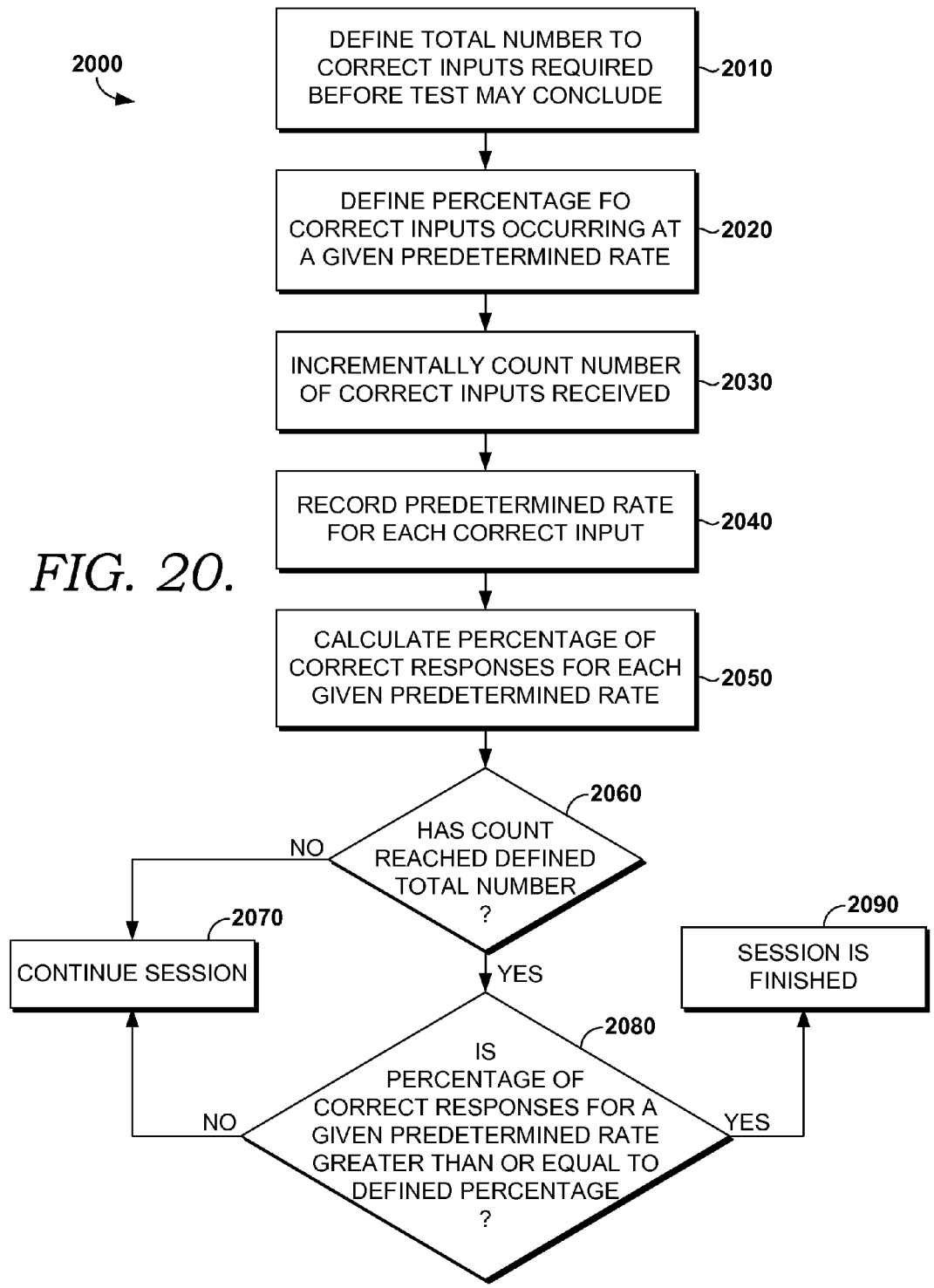
FIG. 20 illustrates a further method in accordance with the present invention for testing and/or training the dynamic visual acuity of a subject.

Referring now to FIG. 20, a further method 2000 of testing and/or training the dynamic visual acuity of a subject is illustrated. In step 2010 a total number of correct inputs required before the session may be concluded is defined. In step 2020 a percentage of correct inputs occurring at a given predetermined rate is defined. In step 2030 iterations are incrementally counted if correct. In step 2040 the predetermined rate of indicia movement for each correct input counted in step 2030 is recorded. In step 2050 the percentage of correct responses for each given predetermined rate is calculated. In step 2060 method 2000 determines whether the count has reached the defined total number of correct inputs. If the conclusion of step 2060 is that the count has not reached the defined total number, method 2000 proceeds to continue the test in step 2070 and will thereafter continue incrementing the total correct count as correct inputs are received. If the conclusion of step 2060 is that the count has reached the defined total number of correct responses method 2000 will proceed to step 2080. In step 2080, method 2000 may determine whether the percentage of correct responses for a given predetermined rate is greater than or equal to the percentage defined in step 2020. If the conclusion of step 2080 is that the percentage of correct responses has not reached the predetermined percentage method 2000 will proceed to step 2070 to continue the test. If the conclusion of step 2080 is that the percentage of correct responses for a given predetermined rate has reached or exceeded the defined percentage method 2000 will proceed to step 2090 to conclude that the test is finished.

Figure 21:
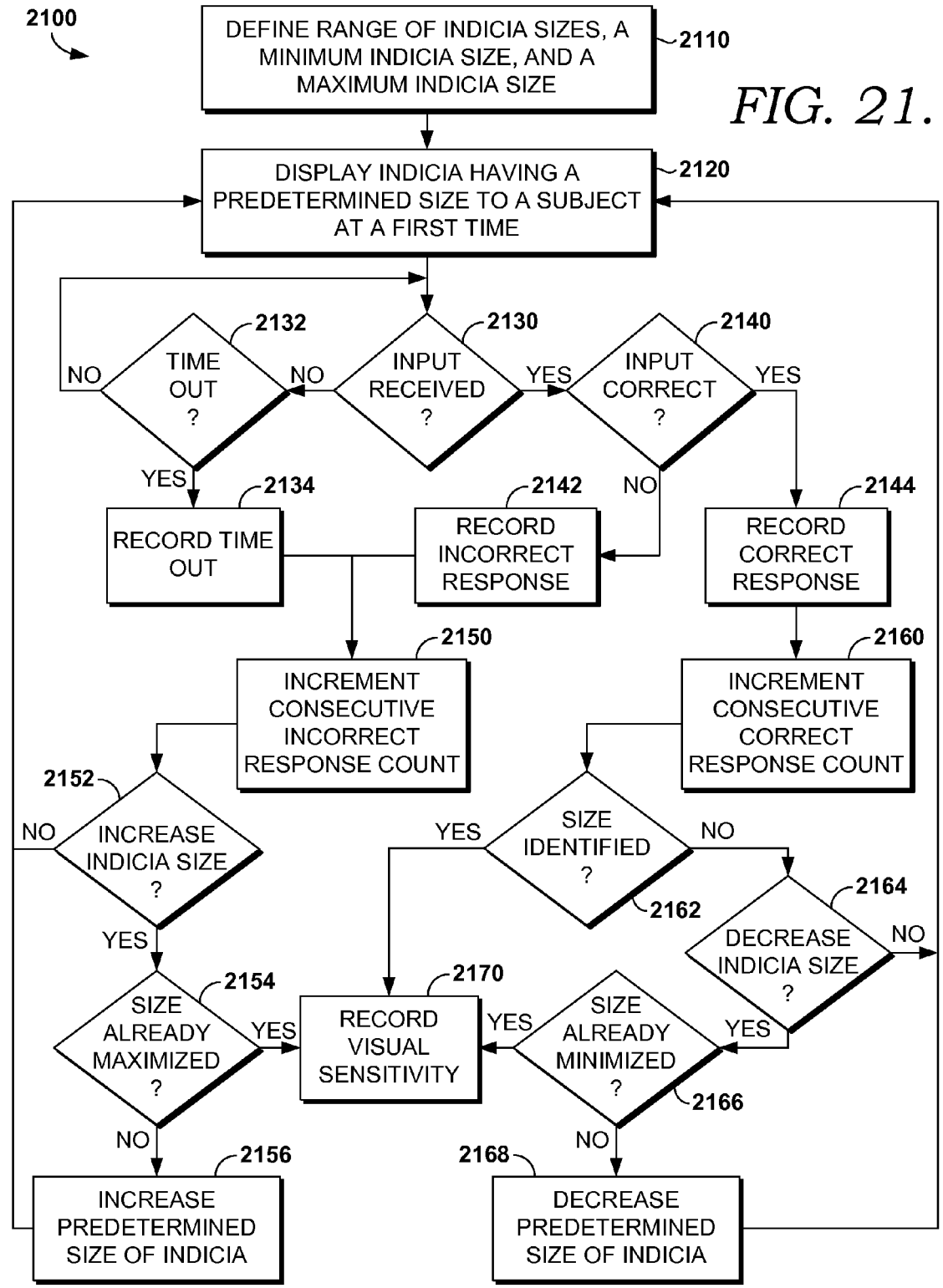
FIG. 21 illustrates a further method in accordance with the present invention for testing and/or training the visual sensitivity of a subject.

Referring now to FIG. 21, a further method 2100 in accordance with the present invention for testing and/or training visual sensitivity using adaptable indicia is illustrated. In step 2110 a range of indicia sizes, a minimum indicia size, and a maximum indicia size may be defined. The definition in step 2110 may be in terms of number of pixels, absolute physical size of an indicia on a display device, visual field occupied by the indicia from the point of view of a subject, or any other way of denoting size of an indicia. In step 2120 an indicia having a predetermined size is displayed to a subject at a first time. After the display of an indicia in step 2120, method 2100 proceeds to step 2130 to determine whether an input has been received. If no input has been received, step 2132 determines whether a timeout has occurred. The duration of time during which a system in accordance with the present invention may wait to receive an input from a subject before a timeout occurs may vary based upon the desires of the subject, the desires of those providing the visual sensitivity testing and/or training, the skill level of a subject, or other factors. If the conclusion of step 2132 is that no timeout has occurred, method 2100 may continue waiting to receive an input in step 2130. If the conclusion of step 2132 is that a timeout has occurred, method 2100 may proceed to record the timeout on a storage device. Step 2134 of recording the timeout condition may also record the circumstances of the timeout, such as the size of the displayed indicia, the orientation or other trait possessed by the displayed indicia, information identifying the subject participating in the testing and/or training, or any other information. If the conclusion of step 2130 is that input has been received, method 2100 may proceed to step 2140 to determine whether that input was correct. For example, an input may correctly identify a trait possessed by a displayed visual indicia. If the input was incorrect, method 2100 may proceed to step 2142 to record the incorrect response. Similarly to step 2134 of recording a timeout, step 2142 of recording an incorrect response may further record additional information regarding the circumstances and time at which the incorrect response was received. After either of steps 2134 and step 2142, method 2100 may proceed to step 2150 to increment a consecutive incorrect response count, should such a count be desired. An incorrect response count, such as may be incremented and kept in step 2150, may be used to determine whether or not to increase an indicia size or ultimately conclude that testing and/or training have reached the minimum visual threshold of an individual. Method 2100 may then proceed to step 2152 to determine whether to increase indicia size. Step 2152 may be based, for example, upon the number of consecutive incorrect responses that have been provided by a subject at a given indicia size. For example, if less than two consecutive incorrect responses have been given by a subject, step 2152 may determine not to increase the size of a displayed indicia for further iterations of method 2100, in which case method 2100 may return to step 2120 of displaying an indicia having the same predetermined size. If the conclusion of step 2152 is that the indicia size should be increased, method 2100 may proceed to step 2154 to determine whether the indicia size is already maximized, as previously defined in step 2110. If the conclusion of step 2154 is that the indicia size is already maximized, method 2100 may proceed to step 2170 of recording the visual sensitivity of the subject as being no better than that corresponding to accurately perceiving the largest maximum defined indicia size. If the conclusion of step 2154 is that the indicia size is not already maximized, method 2100 may proceed to step 2156 of increasing the predetermined size of an indicia. After increasing the predetermined size of an indicia in step 2156, method 2100 may return to step 2120 of displaying an indicia having a predetermined size using the indicia of increased size as defined by step 2156. Step 2156 may determine the amount of size increase of an indicia in any of a variety of fashions, such as using a stair step function similar to that described in FIG. 5B.

If, however, the conclusion of step 2140 is that a correct input has been received, method 2100 may proceed to step 2144 and record the correct response. Step 2144 may record additional information regarding the circumstances and time of the correct response, similarly to the recording of steps 2134 and 2142. Method 2100 may then proceed to step 2160 of incrementing the consecutive correct response count. Similar to the consecutive incorrect response count incremented and maintained in step 2150, the incremental consecutive correct response count incremented and maintained in step 2160 may be utilized to determine when to increase the size of a displayed visual indicia and/or when to determine that the visual sensitivity of the subject has been determined for testing and/or training purposes. For example, method 2100 may proceed to step 2162 to determine whether the size defining the visual sensitivity of the subject has been identified. Step 2162 may, for example, utilize prior recorded correct, incorrect, and timeout responses to conclude that the size of the indicia for the last correct response cannot be reduced without reaching a size at which the subject has provided one or more incorrect responses. If the conclusion of step 2162 is that the size of the indicia defining the visual sensitivity of the subject has been identified, method 2100 may proceed to step 2170 of recording that visual sensitivity. If the conclusion of step 2162 is that the size of the visual indicia defining the visual sensitivity of the subject has not yet been identified, method 2100 may proceed to step 2164 of determining whether to decrease the indicia size. Step 2164 may, for example, utilize the consecutive response count incremented in step 2160 to decrease the size of the next displayed indicia only if a predetermined number of consecutive responses, such as the two consecutive correct responses in the example illustrated previously in FIG. 5B, have been received. If the conclusion of step 2164 is that the indicia size should not be decreased, method 2100 may return to step 2120 of displaying an indicia having the predetermined size. If the conclusion of step 2164 is that the indicia size should be further decreased, method 2100 may proceed to step 2166 to determine whether the indicia size has already reached the minimum size defined previously in step 2110. If the conclusion of step 2166 is that the indicia size is not already minimized, method 2100 may proceed to step 2168 of decreasing the predetermined size of the indicia. Step 2168 may determine the size of the decrease in any of a variety of fashions, such as in the step-wise approach illustrated in the example of FIG. 5B previously. After decreasing the predetermined size of the indicia in step 2168, method 2100 may return to step 2120 of displaying an indicia having a predetermined size using the newly decreased predetermined size determined in step 2168. If the determination of step 2166 is that the indicia size has already been minimized, method 2100 may return to step 2170 of recording the visual sensitivity of the subject as being at worst that defined by the minimum indicia size. Of course, the various steps illustrated as part of exemplary method 2100 may be varied in order, and some may be omitted entirely.

Figure 22:
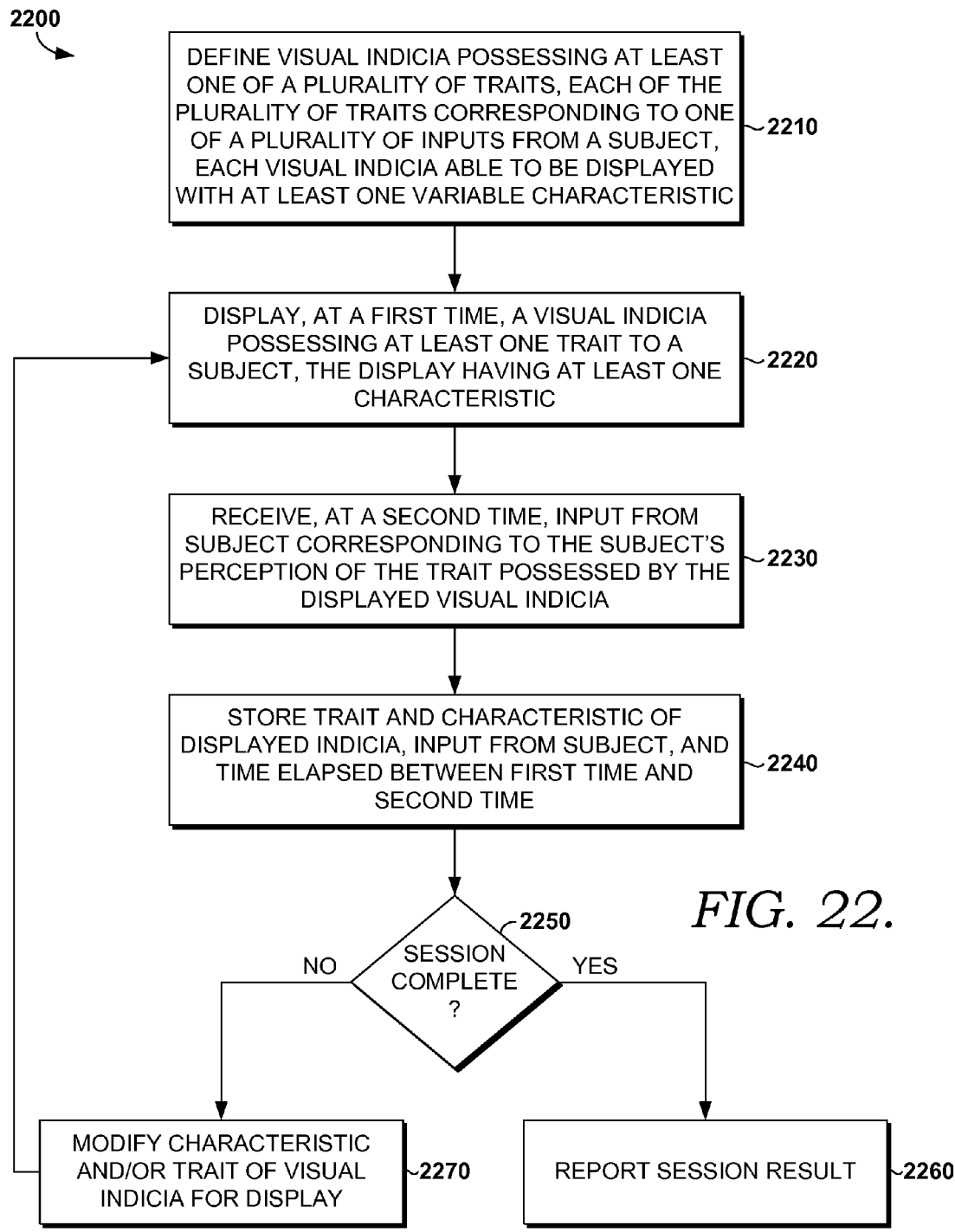
FIG. 22 illustrates a further method in accordance with the present invention for testing and/or training the visual sensitivity of a subject.

Referring now to FIG. 22, a further method 2200 of testing and/or training the visual sensitivity of a subject using adaptable indicia is illustrated. In step 2210, visual indicia possessing at least one of a plurality of traits, each of the plurality of traits corresponding to one of a plurality of inputs from a subject and each visual indicia able to be displayed with at least one variable characteristic may be defined. For example, the visual trait defined for indicia in step 2210 may comprise the orientation of a Landolt C, the identity of a letter or other displayed image, etc. The characteristic of a visual indicia defined in step 2210 may be characteristics such as the visual size of the indicia, the duration of display of the indicia, the location of the indicia on a display device, the contrast of the indicia relative to a visual background, the color of the indicia, the state of motion of the indicia, etc. Method 2200 may then proceed to step 2220 of displaying, at a first time, a visual indicia possessing at least one trait to a subject and having at least one characteristic. Method 2200 may then proceed to step 2230 of receiving, at a second time, an input from the subject corresponding to the subject's perception of the trait possessed by the displayed visual indicia. Step 2230 may include determining that a timeout has occurred due to the failure of a subject to respond to a displayed indicia during a predetermined amount of time. In step 2240, the trait and characteristic of the displayed indicia may be stored, as well as the input from the subject, and the time elapsed between the first time at which the indicia was displayed and the second time at which the input was received from the subject. If a timeout condition was received in step 2230, that information may be recorded as well in step 2240. Further, step 2240 may record and store additional information regarding the testing and/or training iteration, such as the identity of the subject, the time of day, other visual properties associated with the testing and/or training session, etc. Method 2200 may proceed to step 2250 to determine whether the session of testing and/or training is complete. If the conclusion of step 2250 is that the session is complete, method 2200 may proceed to step 2260 to provide a report of the session result. The report generated in step 2260 may describe the performance of the subject during testing and/or training in any degree of detail, including an evaluation of the visual sensitivity of the subject obtained through the use of method 2200. The report generated in step 2260 may comprise a data base entry on a storage device, any other type of electronic record in any kind of volatile or non-volatile electronic memory device, a summary of performance provided on the same display device used for method 2200, a summary of information displayed on any other display device, a physical printout of results on paper or other media, or any other type of report. If the conclusion of step 2250 is that the session was not complete, method 2200 may proceed to step 2270 of modifying a visual characteristic and/or trait of the visual indicia for display. With the modified characteristic and/or trait of the visual indicia from step 2270, method 2200 may return to step 2220 of displaying a visual indicia at a first time possessing the modified characteristic and/or trait.

The examples provided herein merely serve to illustrate some aspects of the present invention. For example, a variety of indicia, including letters, digits, pictures of common everyday objects, and the like may be utilized as a visual indicia. Further, any number of methods and approaches to determining at what size an indicia is being most accurately perceived by a subject may be utilized, and similarly a variety of methods and approaches may be used to determine the speed at which an individual may correctly perceive an indicia. Further, a displayed indicia may possess multiple visual traits, the perception of the desired trait may be part of the testing in

Having thus described the invention, what is claimed is:

1. A system for visual testing and/or training, the system comprising:
   a display device capable of rendering at least one visual indicia during at least a first period of time, each of the at least one visual indicia possessing at least one visual trait defining an orientation of the visual indicia;
   a control unit operably connected to the display device, the control unit operable to cause the display device to render at least one visual indicia possessing at least one visual trait defining an orientation during at least a first period of time, a location of the rendered visual indicia changing at a rate of speed during the first period of time while maintaining the orientation; and
   an input device capable of receiving an input from an individual indicating an orientation defined by a visual trait the individual perceives the rendered visual indicia to possess during the first period of time as the location of the rendered visual indicia changes, the rate of speed of change from a first location to a second location corresponds with a recorded result for the input from the individual, the input device operably connected to the control unit to transmit the received input to the control unit.

2. The system of claim 1, wherein the at least one visual indicia is comprised of a Landolt C.

3. The system of claim 1, wherein the at least one visual trait defining the orientation of the visual indicia is one of four mutually exclusive orientations.

4. The system of claim 1, wherein the rate of speed increases during the first period of time.

5. A method for testing and/or training the visual sensitivity of a subject, the method comprising:
   (a) displaying, at a first location, a visual indicia possessing a visual trait defining an orientation of the visual indicia to a subject;
   (b) displaying, at a second location, the visual indicia possessing the visual trait defining the orientation of the visual indicia;
   (c) receiving an input from the subject indicating that the subject perceived the visual indicia possessing the visual trait, the input being dependent upon an orientation of the visual indicia perceived by the subject;
   (d) comparing the visual trait possessed by the displayed visual indicia to the input received from the subject to determine whether the input corresponds to the visual trait possessed by the visual indicia; and
   (e) recording a rate at which the visual indicia moves from the first location to the second location and recording whether the input corresponds to the visual trait possessed by the visual indicia such that the rate at which the visual indicia moves from the first location to the second location corresponds with a recorded result for the input from the subject.

6. The method for testing and/or training the visual sensitivity of a subject of claim 5, further comprising iteratively repeating steps (a)-(e) a predetermined number of times.

7. The method for testing and/or training the visual sensitivity of a subject of claim 5, further comprising iteratively repeating steps (a)-(e) until a predetermined number of subject-provided inputs have been.

8. The method for testing and/or training the visual sensitivity of a subject of claim 5, further comprising iteratively repeating steps (a)-(e) until the received inputs that correspond to the visual trait possessed by the visual indicia occur at a given rate for a predefined number of occurrences.

9. The method of claim 5, wherein the visual indicia is a Landolt C.

10. The method of claim 5, wherein visual trait defining the orientation of the visual indicia is one of four mutually exclusive orientations.

11. The method of claim 5, wherein a path traveled by the visual indicia between the first location and the second location is non-linear.

12. A visual sensitivity testing and/or training system for testing the visual acuity of an individual, the visual sensitivity testing and/or training system comprising:
    a display device oriented so as to be visually perceived by the individual;
    an input device operable to receive at any given time one of a plurality of possible inputs from the individual;
    a control unit operably connected to the display device and to the input device, the control unit comprising at least one computer readable media having embodied thereon computer readable instructions executed by the testing unit, the computer readable instructions causing the control unit to:
       operate the display device to cause the display device to sequentially display a plurality of visual indicia, each of the plurality of visual indicia possessing one of a plurality of visual traits corresponding to one of the plurality of inputs the input device is operable to receive, each of the plurality of visual indicia being initially displayed at a first time having a first rate of speed moving from a first location to a second location;
       receive inputs from the input device, each input being one of the plurality of inputs the input device is operable to receive;
       operate the display device to cause the display device to increase the rate of speed of each of the plurality of sequentially displayed visual indicia until the control unit receives an input from the input device or the rate of speed of the displayed visual indicia exceeds a predetermined threshold;
       determine whether an input received from the input device corresponding to the visual trait of the visual indicia displayed on the display device when the input was received;
       determine the rate of speed of the visual indicia displayed on the display device when the input was received;
       store whether an input corresponding to the visual trait of the visual indicia displayed on the display device was received; and
       store the rate of speed of the displayed visual indicia when an input was received from the input device.

13. The visual sensitivity testing and/or training system of claim 12, wherein the plurality of visual indicia are comprised of a Landolt C.

14. The visual sensitivity testing and/or training system of claim 12, wherein the plurality of orientations consists of four mutually exclusive orientation.

* * * * *